United States Patent
Fujita et al.

(10) Patent No.: US 8,653,466 B2
(45) Date of Patent: Feb. 18, 2014

(54) SOLID-STATE IMAGING DEVICE AND METHOD OF MANUFACTURING THE SAME, RADIOLOGICAL IMAGING APPARATUS AND METHOD OF MANUFACTURING THE SAME, AND METHOD OF TESTING SOLID-STATE IMAGING DEVICE

(75) Inventors: Kazuki Fujita, Hamamatsu (JP); Ryuji Kyushima, Hamamatsu (JP); Harumichi Mori, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 200 days.

(21) Appl. No.: 13/256,896

(22) PCT Filed: Mar. 26, 2010

(86) PCT No.: PCT/JP2010/055420
§ 371 (c)(1),
(2), (4) Date: Sep. 30, 2011

(87) PCT Pub. No.: WO2010/113811
PCT Pub. Date: Oct. 7, 2010

(65) Prior Publication Data
US 2012/0012753 A1    Jan. 19, 2012

(30) Foreign Application Priority Data
Apr. 1, 2009    (JP) ................ 2009-089257

(51) Int. Cl.
*G01T 1/20*    (2006.01)
*H01L 27/00*    (2006.01)
*H01L 27/146*    (2006.01)

(52) U.S. Cl.
USPC .............. 250/369; 250/208.1; 257/443

(58) Field of Classification Search
USPC ................ 250/369, 208.1; 257/443
See application file for complete search history.

(56) References Cited

U.S. PATENT DOCUMENTS

| | | | | |
|---|---|---|---|---|
| 4,965,671 A | * | 10/1990 | Dielhof | 348/296 |
| 5,396,289 A | * | 3/1995 | Nakamura | 348/294 |
| 2006/0210012 A1 | * | 9/2006 | Yamaguchi et al. | 377/64 |
| 2007/0045552 A1 | * | 3/2007 | Masazumi | 250/370.09 |

FOREIGN PATENT DOCUMENTS

| | | |
|---|---|---|
| CN | 1720435 | 1/2006 |
| EP | 1 568 983 | 8/2005 |
| JP | 60-55660 | 3/1985 |

(Continued)

*Primary Examiner* — David Porta
*Assistant Examiner* — Mindy Vu
(74) *Attorney, Agent, or Firm* — Drinker Biddle & Reath LLP

(57) ABSTRACT

A solid-state imaging device according to one embodiment includes a plurality of signal output units. Each of the plurality of signal output units includes a first input terminal electrode group that includes a plurality of terminal electrodes for inputting a reset signal, a hold signal, a horizontal start signal, and a horizontal clock signal and a first output terminal electrode that provides output signals. The solid-state imaging device further includes a second input terminal electrode group that includes a plurality of terminal electrodes for receiving the reset signal, the hold signal, the horizontal start signal, and the horizontal clock signal, a plurality of switches that switch an electrode group which is connected with integrating circuits, holding circuits, and a horizontal shift register between the first input terminal electrode group and the second input terminal electrode group, and a second output terminal electrode.

17 Claims, 14 Drawing Sheets

(56) References Cited

FOREIGN PATENT DOCUMENTS

| | | |
|---|---|---|
| JP | 4-242974 | 8/1992 |
| JP | 2001-8237 | 1/2001 |
| JP | 2003-319270 | 11/2003 |
| JP | 2006-128244 | 5/2006 |
| JP | 2008-177251 | 7/2008 |
| JP | 2008-270650 | 11/2008 |
| WO | 2008/087907 | 7/2008 |

* cited by examiner

*Fig.9*
(a)
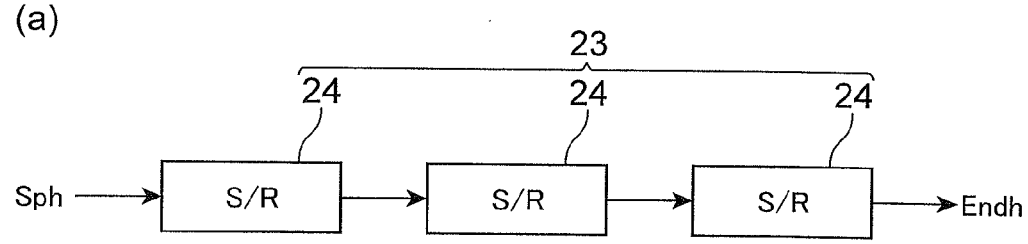
(b)
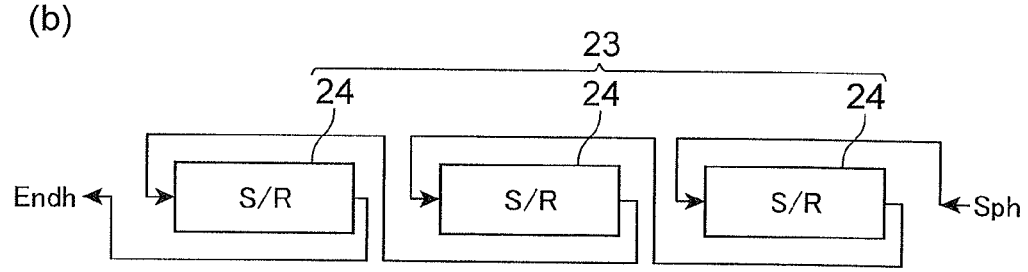

Fig.10
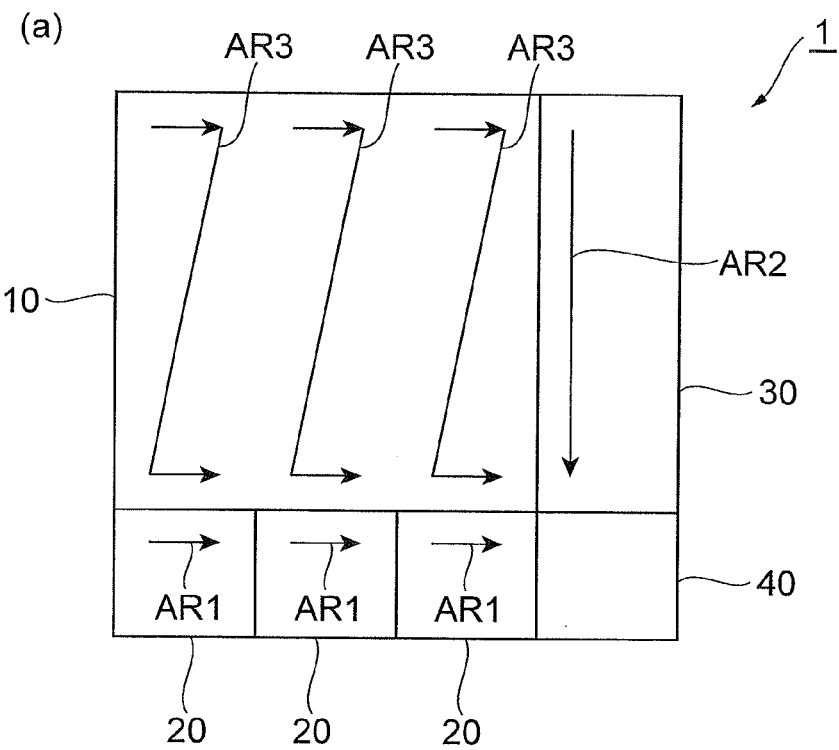
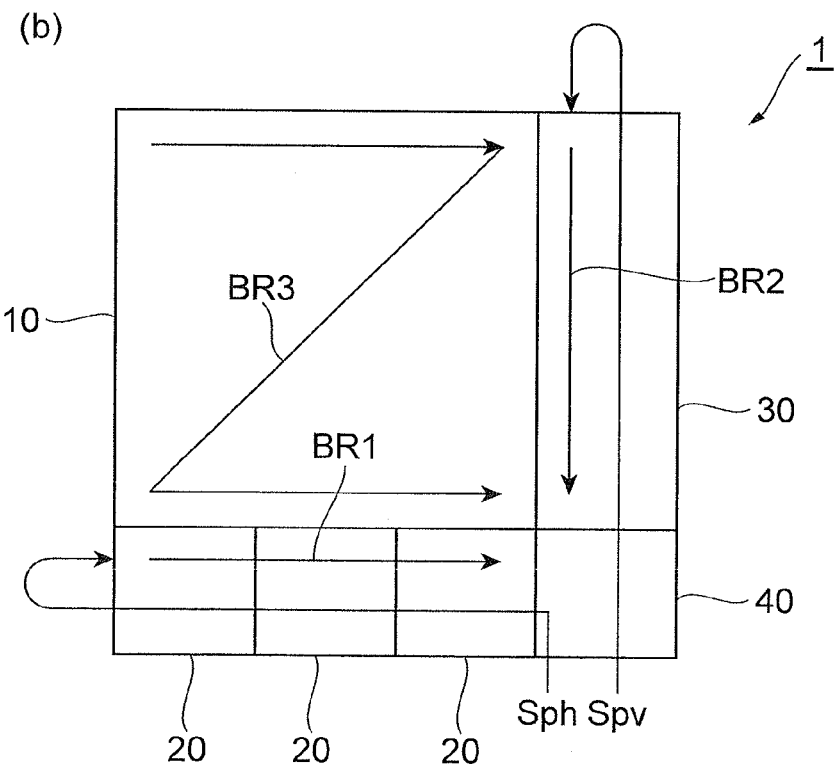

Fig.11
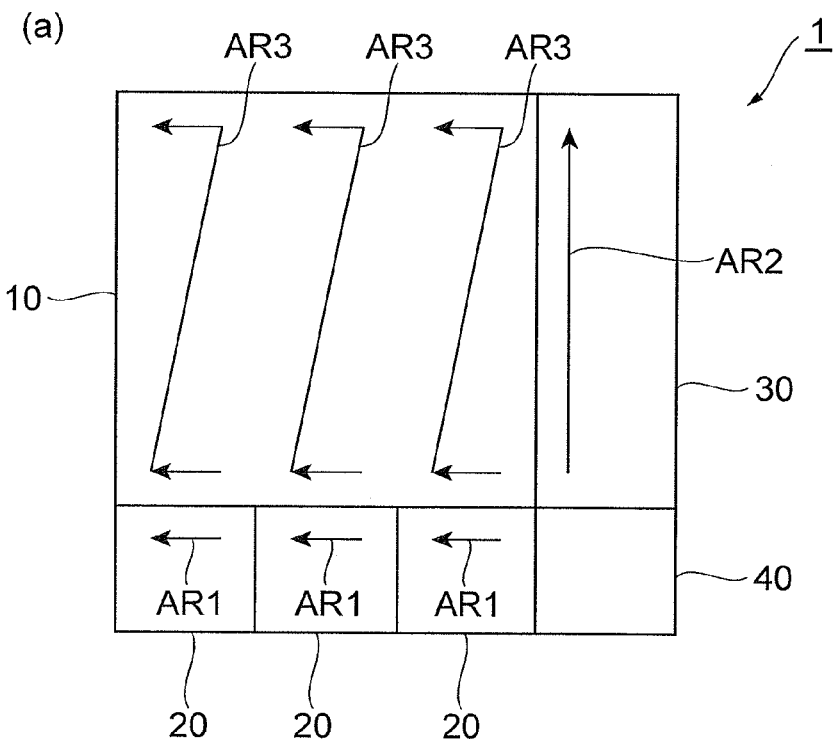
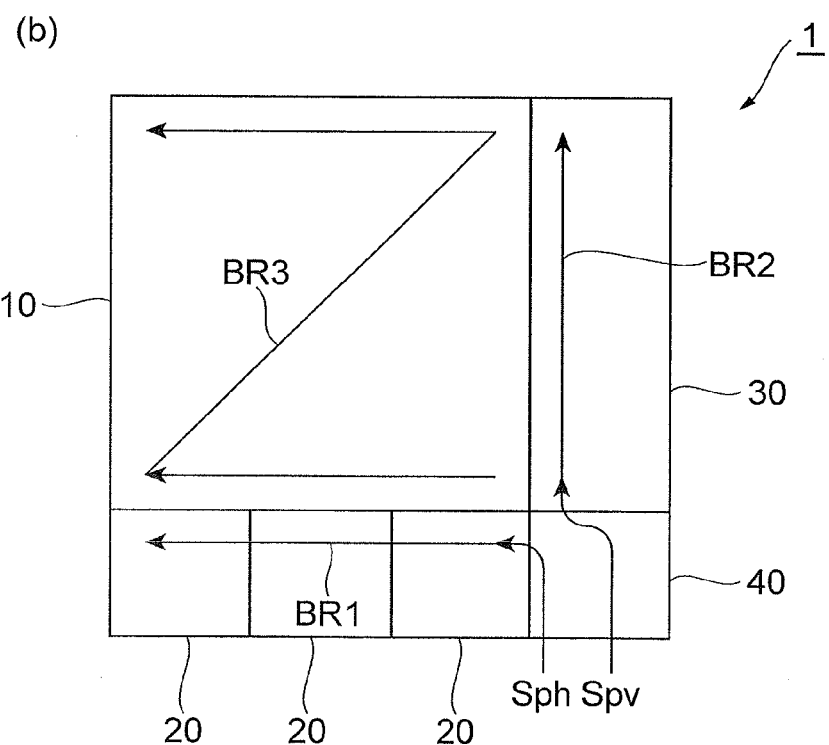

SOLID-STATE IMAGING DEVICE AND METHOD OF MANUFACTURING THE SAME, RADIOLOGICAL IMAGING APPARATUS AND METHOD OF MANUFACTURING THE SAME, AND METHOD OF TESTING SOLID-STATE IMAGING DEVICE

TECHNICAL FIELD

The present invention relates to a solid-state imaging device and a method of manufacturing the same, a radiological imaging apparatus and a method of manufacturing the same, and a method of testing a solid-state imaging device.

BACKGROUND ART

Solid-state imaging devices using a CMOS technique have been known. Among them, a passive-pixel-sensor (PPS) solid-state imaging device has been known. The PPS solid-state imaging device includes a light receiving unit in which PPS pixels, each having a photodiode that generates an amount of charge corresponding to intensity of incident light, are two-dimensionally arranged in a matrix of M rows and N columns. Each pixel accumulates the charge generated in the photodiode responsive to incident light and outputs a voltage value corresponding to the amount of accumulated charge as pixel data.

In general, M pixels in each column are connected to an integrating circuit through a readout line that is provided in association with the column. The voltage value output from the integrating circuit is held once and is sequentially output while being controlled by a shift register.

The PPS solid-state imaging device is used for various purposes. For example, the PPS solid-state imaging device is combined with a scintillator unit to form an X-ray flat panel and is used for medical or industrial purposes. Specifically, the PPS solid-state imaging device is used in, for example, an X-ray CT apparatus or a micro focus X-ray inspection apparatus.

During the manufacture of the PPS solid-state imaging device, in general, test probes are placed on terminal electrodes to check the operation of, for example, the light receiving unit, the integrating circuit, or the shift register. For example, Patent Literature 1 discloses a technique for improving the shape of a pad in order to bring the probes into contact with the pads (terminal electrodes) with high accuracy during the test of the solid-state imaging device. In addition, Patent Literature 2 discloses a method of determining whether each element is defective with a probe test, when a plurality of MOS solid-state imaging devices is formed on one semiconductor wafer.

Patent Literature 3 discloses a technique that injects charge into a photodiode of each pixel in the CMOS image sensor, thereby checking the function without emitting light.

CITATION LIST

Patent Literature

Patent Literature 1: Japanese Patent Application Laid-Open No. 2003-319270
Patent Literature 2: Japanese Patent Application Laid-Open No. 2001-8237
Patent Literature 3: Japanese Patent Application Laid-Open No. 2006-128244

SUMMARY OF INVENTION

Technical Problem

When the solid-state imaging device is used in, for example, the X-ray CT apparatus, a light receiving unit with a large area of 12 cm square may be needed. In such a case, in order to manufacture, for example, a large-area light receiving unit or an integrating circuit corresponding to the light receiving unit, a region on the semiconductor wafer is divided into a plurality of regions and a semiconductor structure is formed in each region using a corresponding mask. For example, a plurality of circuit units (hereinafter, referred to as signal output units) each having an integrating circuit or a shift register are provided in association with respective column groups that are divided from N columns in the light receiving unit. The plurality of circuit units is formed so as to have the same structure. Therefore, a number of terminal electrodes for inputting the reset signal of the integrating circuit or the clock signal of the shift register and a number of terminal electrodes for extracting output signals are provided in association with respective column group.

In the solid-state imaging device, for example, during the test of the light receiving unit or the integrating circuit, in the method disclosed in Patent Literature 1 and Patent Literature 2 in which the probes are placed on the terminal electrodes, it is necessary to bring a number of probes into contact with the terminal electrodes at the same time. However, it is difficult to align the positions of the leading ends of the plurality of probes. Therefore, in the method, for example, a contact failure is likely to occur between the probes and the terminal electrodes, which makes it difficult to accurately perform the test.

The present invention has been created to solve the aforementioned problem and an object of the present invention is to allow for more accurate and easier testing of a light receiving unit, an integrating circuit, and the like in a large-area solid-state imaging device and a method of manufacturing the same, a radiological imaging apparatus including the large-area solid-state imaging device and a method of manufacturing the same, and a method of testing a large-area solid-state imaging device.

Solution to Problem

According to one embodiment of the present invention, there is provided a solid-state imaging device including: a light receiving unit that includes M×N (M and N are integers equal to or greater than 2) pixels which are two-dimensionally arranged in a matrix of M rows and N columns and each of which includes a photodiode; a plurality of signal output units that are provided in association with a plurality of column groups, respectively, wherein the column groups are divided from the N columns and each of the column groups includes two or more columns; and a vertical shift register that controls charge outputs from the pixels on row by row basis. That is, the light receiving unit includes M×N pixels. The M×N pixels are arranged in a matrix of M rows and N columns. The light receiving unit includes a plurality of column groups. Each of the plurality of column groups includes two or more different pixel columns different from each other. Each of the plurality of signal output units includes two or more integrating circuits, two or more holding circuits, a horizontal shift register, a first input terminal electrode group, and a first output terminal electrode. The two or more integrating circuits are provided in association with two or more columns in the corresponding column group, respectively, accumulate charge output from the pixels in the corresponding column, and convert the charge into a voltage signal. The two or more holding circuits are connected to output ends of the two or more integrating circuits, respectively. The horizontal shift register causes the two or more holding circuits to sequentially output voltage signals. The first input terminal electrode group includes a plurality of terminal electrodes. The plurality of terminal electrodes is for inputting a reset signal that resets the integrating circuits, a hold signal that controls the input of voltage signals to the holding circuits, a horizontal start signal that starts the operation of the horizontal shift register, a horizontal clock signal that regulates the clock of the horizontal shift register. The first output terminal electrode provides output signals from the holding circuits. The solid-state imaging device further includes a second input terminal electrode group, input switches, a second output terminal electrode, an input signal line, and an output signal line. The second input terminal electrode group is provided separately from the first input terminal electrode group and includes a plurality of terminal electrodes. The plurality of terminal electrodes is for receiving the reset signal, the hold signal, the horizontal start signal, and the horizontal clock signal, respectively. The input switches are provided in each signal output unit in order to switch an electrode group which is connected with the integrating circuits, the holding circuits, and the horizontal shift register, between the first and second input terminal electrode groups. The second output terminal electrode is provided separately from the first output terminal electrode and provides the output signal. The input signal line is provided across the plurality of signal output units in order to connect the input switches in each signal output unit with the second input terminal electrode group (except for a terminal electrode for the horizontal start signal). The output signal line is provided across the plurality of signal output units in order to connect the holding circuits in each signal output unit with the second output terminal electrode.

The solid-state imaging device includes the second input terminal electrode group that is provided separately from the first input terminal electrode group provided in each signal output unit, as a plurality of terminal electrodes for inputting the reset signal to the integrating circuit, the hold signal to the holding circuit, the horizontal start signal to the horizontal shift register, and the horizontal clock signal for regulating the clock of the horizontal shift register. Similarly, the solid-state imaging device includes the second output terminal electrode that is provided separately from the first output terminal electrode for providing the output signal.

In the solid-state imaging device, when the operation of the light receiving unit, the integrating circuit, the holding circuit, and the horizontal shift register is tested, the input switches are switched to the second input terminal electrode group. When the test probes are brought into contact with the second input terminal electrode group, the reset signal, the hold signal, the horizontal start signal, and the horizontal clock signal given to the second input terminal electrode group are provided to the integrating circuits, the holding circuits, and the horizontal shift register through the input signal line provided across the plurality of signal output units, respectively. The output signals obtained by the above-mentioned process are extracted from the second output terminal electrode through the output signal line which is provided across the plurality of signal output units.

When the solid-state imaging device performs a normal operation, the input switch is switched to the first input terminal electrode. Then, the reset signal, hold signal, the horizontal start signal, and the horizontal clock signal are given to the first input terminal electrode group in each signal output unit. The output signals obtained by the above-mentioned process are extracted from the first output terminal electrode in each signal output unit.

As described above, according to the solid-state imaging device of the present invention, the probes are not brought into contact with the first input terminal electrode group and the first output terminal electrode provided in each of the plurality of signal output units, but are brought into contact with the second input terminal electrode group and the second output terminal electrode which are separately provided for a test, thereby testing the operation of the light receiving unit, the integrating circuit and the like. Therefore, the number of probes that are brought into contact with the terminal electrodes is reduced, as compared to a method in which the probes are brought into contact with the terminal electrodes of all of the signal output units simultaneously. As a result, even when the light receiving unit has a large area, it is possible to accurately and easily test the light receiving unit and the plurality of signal output units.

In a solid-state imaging device according to one embodiment, each of the plurality of signal output units may be arranged adjacent to one side of the light receiving unit extending along a row direction. The vertical shift register may be arranged adjacent to another side of the light receiving unit extending along a column direction. The second input terminal electrode group and the second output terminal electrode may be arranged in a region which is adjacent to the signal output unit closest to the vertical shift register among the plurality of signal output units. This arrangement makes it possible to effectively arrange the input signal line and the output signal line and appropriately arrange the second input terminal electrode group and the second output terminal electrode so as not to affect the arrangement of the signal output unit or the vertical shift register.

In a solid-state imaging device according to one embodiment, the terminal electrode for the horizontal start signal in the second input terminal electrode group may be connected to the horizontal shift register of the signal output unit which is disposed at an end among the plurality of signal output units. When the horizontal start signal is input to the terminal electrode, the horizontal shift register of another signal output unit may receive an output from the last stage of the horizontal shift register of an adjacent signal output unit as the horizontal start signal. According to this configuration, the output signals from the plurality of signal output units can be sequentially extracted from the second output terminal electrode. In the solid-state imaging device according to one embodiment, in each of the signal output units, a scanning direction of the horizontal shift register may be variable. For example, during a normal operation, the horizontal shift register performs scanning in a direction approaching to the second input terminal electrode group (particularly, the terminal electrode for the horizontal start signal). In such a case, during the test of the light receiving unit and the signal output units, when the scanning direction of the horizontal shift register is changed to a direction departing away from the second input terminal electrode group, it is possible to reduce the length of a line for connecting the terminal electrode for the horizontal start signal in the second input terminal electrode group and the horizontal shift register of the signal output unit that is disposed at the end.

In a solid-state imaging device according to the one embodiment, each of the plurality of signal output units may further include a first power supply terminal electrode for inputting a power supply voltage. The solid-state imaging device may further include a second power supply terminal electrode that is provided separately from the first power supply terminal electrode provided in each of the plurality of signal output units and receives the power supply voltage. The first and second power supply terminal electrodes may be connected to each other by a line that is provided across the plurality of signal output units. In this way, when the light receiving unit and the plurality of signal output units are tested, the number of probes for supplying the power supply voltage is reduced and it is possible to perform the test with ease.

In one embodiment, the solid-state imaging device may further include an output switch that is provided in each of the signal output units in order to switch connection/disconnection between the holding circuit and the output signal line. According to this configuration, when a given signal output unit outputs a signal, it is possible to disconnect the other signal output units from the output signal line. Therefore, it is possible to prevent an influence on the output signal passing through the output signal line. For example, when the operation of the horizontal shift register starts, the output switch connects the holding circuits with the output signal line. When the operation of the horizontal shift register is completed, the output switch disconnects the holding circuits from the output signal line. As a result, it is possible to effectively obtain the above-mentioned effect.

According to another embodiment of the present invention, there is provided a radiological imaging apparatus including: the solid-state imaging device according to any one of the above-mentioned embodiments; and a scintillator that is provided on the light receiving unit, generates scintillation light according to incident radiation, converts a radiation image into an optical image, and outputs the optical image to the light receiving unit. The radiological imaging apparatus includes the solid-state imaging device according to any one of the above-mentioned embodiments. Therefore, according to the radiological imaging apparatus, it is possible to accurately and easily test the light receiving unit and the signal output units of the solid-state imaging device. As a result, it is possible to provide a radiological imaging apparatus with high reliability.

According to still another embodiment of the present invention, there is provided a method of manufacturing a solid-state imaging device including: a light receiving unit that includes M×N (M and N are integers equal to or greater than 2) pixels which are two-dimensionally arranged in a matrix of M rows and N columns and each of which includes a photodiode; a plurality of signal output units that are provided in association with a plurality of column groups, respectively, wherein the column groups are divided from the N columns and each of the column groups includes two or more columns; and a vertical shift register that controls charge outputs from the pixels on row by row basis. The method of manufacturing a solid-state imaging device includes: a forming step of forming, in each region which will be each of the plurality of signal output units on a semiconductor substrate, two or more integrating circuits that are provided in association with the two or more columns in the corresponding column group, respectively, and each of which accumulates charge output from the pixels in the corresponding column and converts the charge into a voltage signal, two or more holding circuits that are connected to output ends of the two or more integrating circuits, respectively, a horizontal shift register that causes the two or more holding circuits to sequentially output voltage signals, a first input terminal electrode group including a plurality of terminal electrodes for inputting a reset signal that resets the integrating circuits, a hold signal that controls the input of the voltage signals to the holding circuits, a horizontal start signal that starts the operation of the horizontal shift register, and a horizontal clock signal that regulates clock of the horizontal shift register, and a first output terminal electrode that provides output signals from the holding circuits, and forming the light receiving unit and the vertical shift register on the semiconductor substrate; a test step of testing operation of the light receiving unit and the plurality of signal output units and selecting the semiconductor substrate that is normally operated; and a wire bonding step of connecting the first input terminal electrode group and the first output terminal electrode of each signal output unit in the semiconductor substrate selected in the test step to a wiring pattern that is prepared outside the semiconductor substrate, using wire bonding. In the forming step, a second input terminal electrode group including a plurality of terminal electrodes for receiving the reset signal, the hold signal, the horizontal start signal, and the horizontal clock signal is formed separately from the first input terminal electrode group; input switches that switch an electrode group which is connected with the integrating circuits, the holding circuits, and the horizontal shift register between the first and second input terminal electrode groups are formed in each signal output unit; a second output terminal electrode that provides the output signal is formed separately from the first output terminal electrode; and an input signal line that connects the input switches in each signal output unit with the second input terminal electrode group (except for a terminal electrode for the horizontal start signal) and an output signal line that connects the holding circuits in each signal output unit with the second output terminal electrode are formed across the plurality of signal output units. In the test step, the input switches are switched to the second input terminal electrode group; probes are brought into contact with the second input terminal electrode group; the reset signal, the hold signal, the horizontal start signal and the horizontal clock signal are given to the second input terminal electrode group; and another probe is brought into contact with the second output terminal electrode to acquire voltage signals, thereby testing operation of the light receiving unit and the plurality of signal output units.

In the method of manufacturing a solid-state imaging device, in the forming step, the second input terminal electrode group is formed separately from the first input terminal electrode group which is provided in each signal output unit, as a plurality of terminal electrodes for inputting the reset signal to the integrating circuit, the hold signal to the holding circuit, the horizontal start signal to the horizontal shift register, and the horizontal clock signal for regulating the clock of the horizontal shift register. Similarly, the second output terminal electrode is formed separately from the first output terminal electrode for providing the output signal. In the test step, the input switches are switched to the second input terminal electrode group. In this case, when the test probes are brought into contact with the second input terminal electrode group, the reset signal, the hold signal, the horizontal start signal, and the horizontal clock signal given to the second input terminal electrode group are provided to the integrating circuits, the holding circuits, and the horizontal shift register through the input signal line provided across the plurality of signal output units, respectively. The output signals obtained by the above-mentioned process are extracted from the second output terminal electrode through the output signal line which is provided across the plurality of signal output units.

When the solid-state imaging device manufactured by the above-mentioned method performs a normal operation, the input switch is switched to the first input terminal electrode. Then, the reset signal, hold signal, the horizontal start signal, and the horizontal clock signal are given from the wiring pattern that is prepared outside the semiconductor substrate to the first input terminal electrode group in each signal output unit through bonding wires. The output signals obtained by the above-mentioned process are extracted from the first output terminal electrode in each signal output unit through the bonding wire.

As described above, according to the method of manufacturing a solid-state imaging device of the present invention, in the test step, the probes are not brought into contact with the first input terminal electrode group and the first output terminal electrode provided in each of the plurality of signal output units, but are brought into contact with the second input terminal electrode group and the second output terminal electrode which are separately provided for a test, thereby testing the operation of the light receiving unit, the signal output units and the like. Therefore, the number of probes that are brought into contact with the terminal electrodes is reduced. As a result, even when the light receiving unit has a large area, it is possible to accurately and easily test the light receiving unit and the signal output units.

In a method of manufacturing a solid-state imaging device according to one embodiment, in the forming step, each of the plurality of signal output units may be formed adjacent to one side of the light receiving unit extending along a row direction and the vertical shift register may be formed adjacent to another side of the light receiving unit extending along a column direction. In addition, the second input terminal electrode group and the second output terminal electrode may be formed in a region which is adjacent to the signal output unit closest to the vertical shift register among the plurality of signal output units. This arrangement makes it possible to effectively arrange the input signal line and the output signal line and appropriately arrange the second input terminal electrode group and the second output terminal electrode so as not to affect the arrangement of the signal output unit or the vertical shift register.

In a method of manufacturing a solid-state imaging device according to one embodiment, in the forming step, the terminal electrode for the horizontal start signal in the second input terminal electrode group may be connected to the horizontal shift register of the signal output unit which is disposed at an end among the plurality of signal output units. In the test step, the horizontal shift register of another signal output unit may receive an output from the last stage of the horizontal shift register of an adjacent signal output unit as the horizontal start signal. According to the method, the output signals from the plurality of signal output units can be sequentially extracted from the second output terminal electrode. In a method of manufacturing a solid-state imaging device according to one embodiment, in each of the signal output units, the scanning direction of the horizontal shift register in the test step may be different from that of the horizontal shift register in a normal operation. For example, during a normal operation, the horizontal shift register may perform scanning in a direction approaching to the second input terminal electrode group (particularly, the terminal electrode for the horizontal start signal). In this case, in the test step, when the scanning direction of the horizontal shift register is changed to a direction departing away from the second input terminal electrode group, it is possible to reduce the length of a line for connecting the terminal electrode for the horizontal start signal in the second input terminal electrode group and the horizontal shift register of the signal output unit that is disposed at the end.

In a method of manufacturing a solid-state imaging device according to one embodiment, in the forming step, a first power supply terminal electrode for inputting a power supply voltage may be formed in each region which will be each of the plurality of signal output units on the semiconductor substrate, and a second power supply terminal electrode that provides the power supply voltage may be formed separately from the first power supply terminal electrode. In addition, a line that connects the first and second power supply terminal electrodes may be formed across the plurality of signal output units. According to the method, in the test step, the number of probes for supplying the power supply voltage is reduced and it is possible to test the light receiving unit or the signal output units with ease.

In a method of manufacturing a solid-state imaging device according to one embodiment, in the forming step, an output switch for switching connection/disconnection between the holding circuits and the output signal line may be further formed in each region which will be each of the plurality of signal output units on the semiconductor substrate. According to the method, in the test step, when a given signal output unit outputs a signal, it is possible to disconnect the other signal output units from the output signal line. Therefore, it is possible to prevent an influence on the output signal passing through the output signal line. For example, in the test step, when the operation of the horizontal shift register starts, the output switch connects the holding circuits with the output signal line. When the operation of the horizontal shift register is completed, the output switch disconnects the holding circuits from the output signal line. As a result, it is possible to effectively obtain the above-mentioned effect.

According to still another embodiment of the present invention, there is provided a method of manufacturing a radiological imaging apparatus including: the method of manufacturing a solid-state imaging device according to any one of the above-mentioned embodiments; and a scintillator attaching step of providing, on the light receiving unit, a scintillator that generates scintillation light according to incident radiation, converts a radiation image into an optical image, and outputs the optical image to the light receiving unit. The scintillator attaching step is performed before or after the test step. The method of manufacturing a radiological imaging apparatus includes the method of manufacturing a solid-state imaging device according to any one the above-mentioned embodiments. Therefore, according to the method of manufacturing a radiological imaging apparatus, it is possible to accurately and easily test the light receiving unit and the plurality of signal output units of the solid-state imaging device and thus provide a radiological imaging apparatus with high reliability.

According to still yet another embodiment of the present invention, there is provided a method of testing a solid-state imaging device including: a light receiving unit that includes M×N (M and N are integers equal to or greater than 2) pixels which are two-dimensionally arranged in a matrix of M rows and N columns and each of which includes a photodiode; a plurality of signal output units that are provided in association with a plurality of column groups, respectively, wherein the column groups are divided from the N columns and each of the column groups includes two or more columns; and a vertical shift register that controls charge outputs from the pixels on row by row basis. Each of the plurality of signal output units includes: two or more integrating circuits that are provided in association with the two or more columns in a corresponding column group, respectively, accumulate the charge output from the pixels in the corresponding columns, and convert the charge into a voltage signal; two or more holding circuits that are connected to output ends of the two or more integrating circuits, respectively; a horizontal shift register that causes the two or more holding circuits to sequentially output voltage signals; a first input terminal electrode group including a plurality of terminal electrodes for inputting a reset signal that resets the integrating circuit, a hold signal that controls input of the voltage signal to the holding circuits, a horizontal start signal that starts operation of the horizontal shift register, and a horizontal clock signal that regulates clock of the horizontal shift register; and a first output terminal electrode that provides an output signal from the holding circuit. The method of testing a solid-state imaging device includes: forming, separately from the first input terminal electrode group, a second input terminal electrode group including a plurality of terminal electrodes for receiving the reset signal, the hold signal, the horizontal start signal, and the horizontal clock signal; forming, in each signal output unit, input switches that switch an electrode group which is connected with the integrating circuits, the holding circuits, and the horizontal shift register between the first and second input terminal electrode groups; forming, separately from the first output terminal electrode, a second output terminal electrode that provides the output signals; forming an input signal line that connects the input switches in each signal output unit with the second input terminal electrode group (except for a terminal electrode for the horizontal start signal) and an output signal line that connects the holding circuits in each signal output unit and the second output terminal electrode, across the plurality of signal output units; and switching the input switches to the second input terminal electrode group and bringing probes into contact with the second input terminal electrode group to provide the reset signal, the hold signal, the horizontal start signal and the horizontal clock signal to the second input terminal electrode group, and bringing another probe into contact with the second output terminal electrode to acquire the voltage signal, thereby testing operation of the light receiving unit and the plurality of signal output units.

According to the method of testing a solid-state imaging device, similarly to the method of manufacturing a solid-state imaging device, the probes are not brought into contact with the first input terminal electrode group and the first output terminal electrode provided in each of the plurality of signal output units, but are brought into contact with the second input terminal electrode group and the second output terminal electrode which are separately provided for a test, thereby testing the operation of, for example, the light receiving unit and the signal output units. Therefore, the number of probes that are brought into contact with the terminal electrodes is reduced. As a result, even when the light receiving unit has a large area, it is possible to accurately and easily test the light receiving unit and the signal output units.

Advantageous Effects of Invention

According to the present invention, it is possible to accurately and easily test a light receiving unit, an integrating circuit and the like in a large-area solid-state imaging device and a method of manufacturing the same, a radiological imaging apparatus including the large-area solid-state imaging device and a method of manufacturing the same, and a method of testing a solid-state imaging device.

BRIEF DESCRIPTION OF DRAWINGS

FIG. 9 is a block diagram schematically illustrating a horizontal shift register 23 included in each of a plurality of signal output units 20. In (a) of FIG. 9, a case in which a first shift register 24 exists at the left end, that is, the scanning of the horizontal shift register 23 is performed in a direction to the test terminal electrode unit 40, is shown. In (b) of FIG. 9, a case in which the first shift register 24 exists at the right end, that is, the scanning of the horizontal shift register 23 is performed in a direction away from the test terminal electrode unit 40, is shown.

FIG. 10 is a plan view schematically illustrating the aspects of (a) the normal operation mode and (b) the test mode of the solid-state imaging device 1 when the scanning direction of the horizontal shift register 23 is the direction shown in (a) of FIG. 9.

FIG. 11 is a plan view schematically illustrating the aspects of (a) the normal operation mode and (b) the test mode of the solid-state imaging device 1 when the scanning direction of the horizontal shift register 23 is the direction shown in (b) of FIG. 9.

DESCRIPTION OF EMBODIMENTS

Hereinafter, exemplary embodiments of the present invention will be described in detail with reference to the accompanying drawings. In the description of the drawings, the same components are denoted by the same reference symbols and a description thereof will be omitted.

(First Embodiment)

Figure 1:
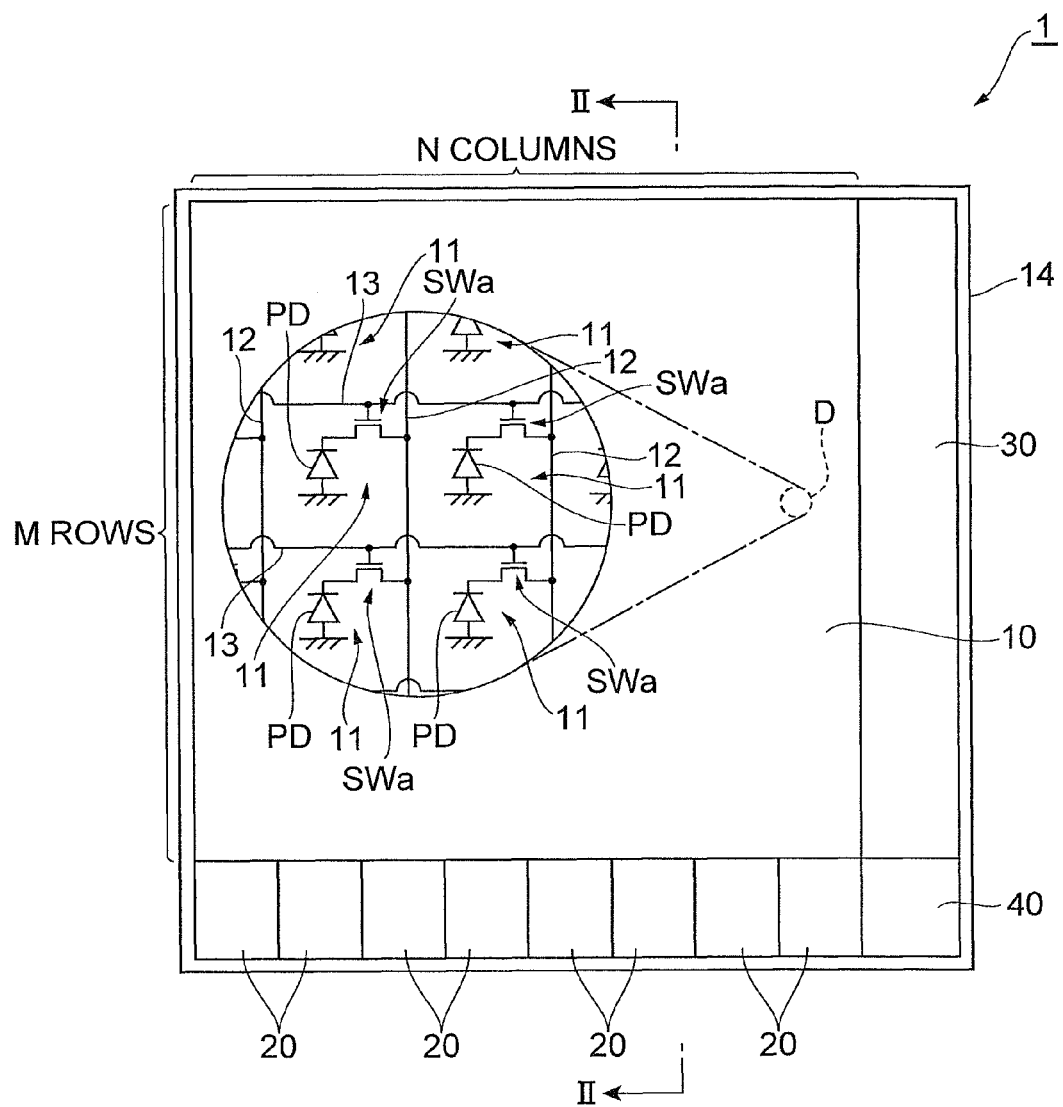
FIG. 1 is a diagram schematically illustrating a structure of a solid-state imaging device 1 according to a first embodiment.
Figure 2:
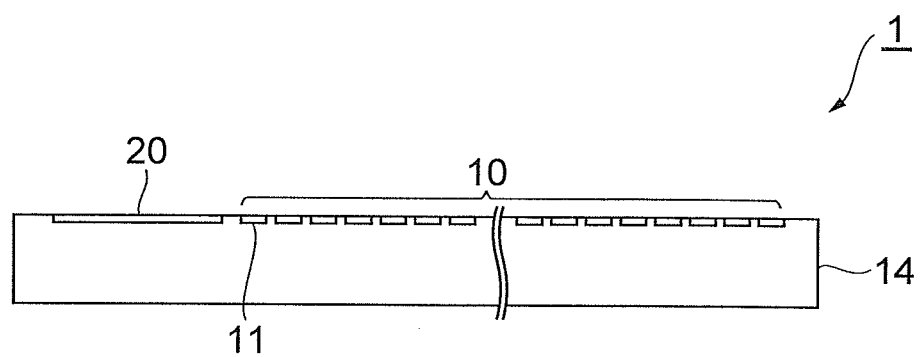
FIG. 2 is a side cross-sectional view illustrating a cross section of the solid-state imaging device 1 taken along the line II-II of FIG. 1.

FIG. 1 is a diagram schematically illustrating a structure of a solid-state imaging device 1 according to an embodiment. FIG. 2 is a side cross-sectional view illustrating a cross section of the solid-state imaging device 1 taken along the line II-II of FIG. 1. The solid-state imaging device 1 according to this embodiment includes a light receiving unit 10, a plurality of signal output units 20, a vertical shift register 30, and a test terminal electrode unit 40. In FIG. 1, a region D of the light receiving unit 10 is enlarged.

As shown in FIG. 1, the plurality of signal output units 20 are arranged adjacent to one side of the light receiving unit 10 extending along a row direction, and the vertical shift register 30 is arranged adjacent to another side of the light receiving unit 10 extending along a column direction. The test terminal electrode unit 40 is arranged in a region adjacent to the signal output unit 20 that is disposed at an end (hereinafter, referred to as a right end) closest to the vertical shift register 30 among the plurality of signal output units 20.

The light receiving unit 10 includes M×N pixels 11. The M×N pixels 11 are two-dimensionally arranged in a matrix of M rows and N columns (where M and N are integers equal to or greater than 2). The pixels 11 are of a PPS type and have the same structure.

The N pixels 11 forming each row of the light receiving unit 10 are connected to the vertical shift register 30 via a row selecting line 13 that is provided in association with to the relevant row. The vertical shift register 30 is provided in order to control charge outputs from the pixels 11 on row by row basis. The M pixels 11 forming each column of the light receiving unit 10 have respective output ends that are connected to one of the plurality of signal output units 20 via a readout line 12 which is provided in association with the relevant column.

Each of the pixels 11 in the light receiving unit 10 includes a photodiode PD and a readout switch SWa. An anode terminal of the photodiode PD is connected to the ground and a cathode terminal of the photodiode PD is connected to the readout line 12 through the readout switch SWa. The photodiode PD generates charge an amount of which corresponds to the intensity of incident light and accumulates the generated charge in a junction capacitor. A row selection control signal is supplied from the vertical shift register 30 to the readout switch SWa through the row selecting line 13. The row selection control signal is for instructing switching operation of the readout switches SWa of the N pixels 11 in each row of the light receiving unit 10.

In each pixel 11, when the row selection control signal is at a low (L) level, the readout switch SWa is open and the charge generated by the photodiode PD is accumulated in the junction capacitor without being output to the readout line 12. On the other hand, when the row selection control signal is at a high (H) level, the readout switch SWa is closed and the charge that has been generated by the photodiode PD and then accumulated in the junction capacitor is output to the readout line 12 through the readout switch SWa.

The light receiving unit 10, the signal output units 20, the vertical shift register 30, and the test terminal electrode unit 40 are provided on the main surface of a semiconductor substrate 14. The semiconductor substrate 14 may be attached to a plate-shaped base material to maintain mechanical strength thereof.

Figure 3:
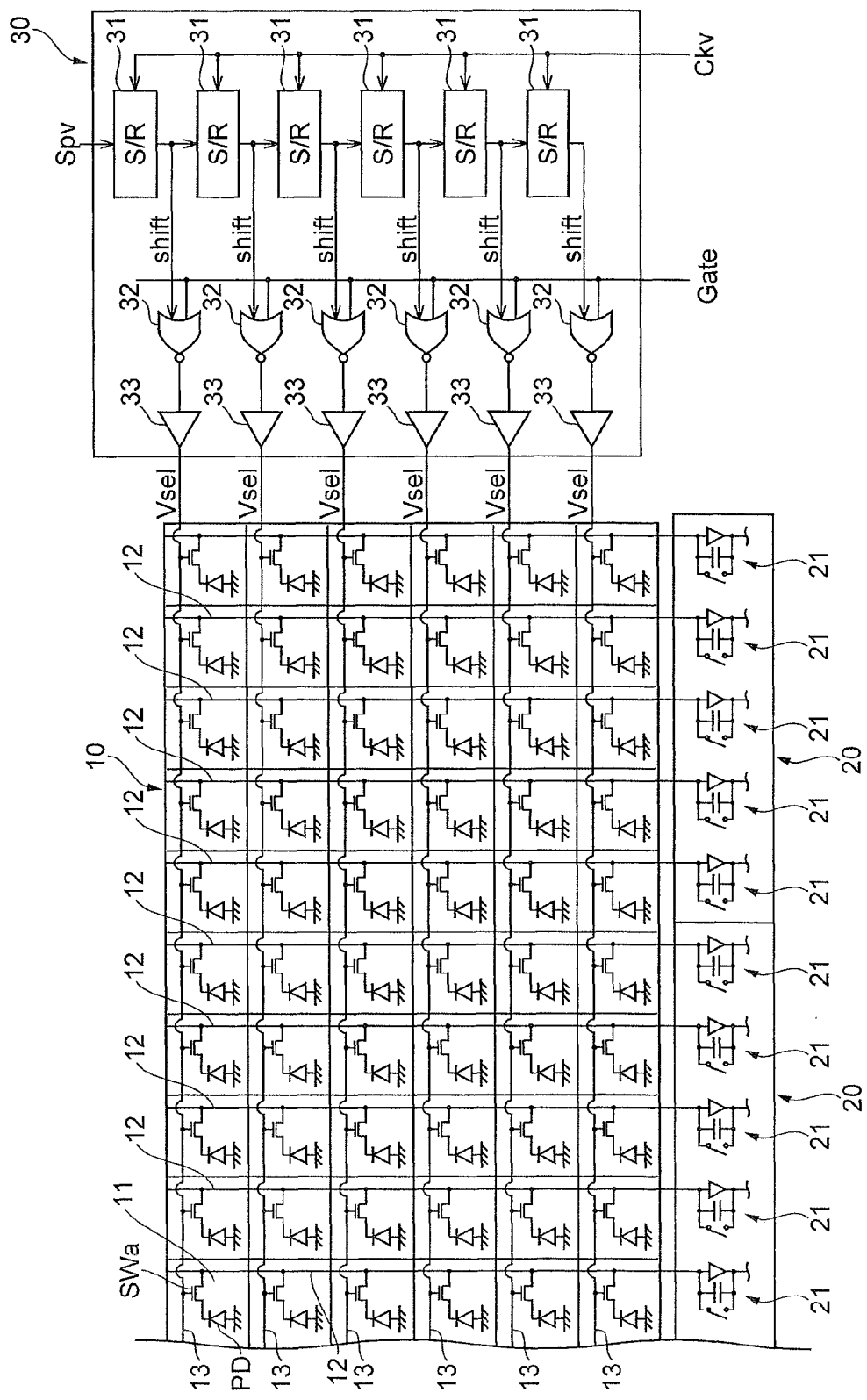
FIG. 3 is a circuit diagram illustrating in detail a structure of some of N columns included in a light receiving unit 10, signal output units 20 corresponding to some columns, and a vertical shift register 30, among components of the solid-state imaging device 1 shown in FIG. 1.

FIG. 3 is a circuit diagram illustrating in detail a structure of some of the N columns in the light receiving unit 10, a structure of the signal output units 20 corresponding to some columns, and a structure of the vertical shift register 30, among the components of the solid-state imaging device 1 shown in FIG. 1.

The vertical shift register 30 includes a plurality of shift registers 31 that are connected in series to each other, and NOR circuits (NOR gates) 32 and buffers 33 that are provided in association with the rows of the light receiving unit 10, respectively. A vertical clock signal Ckv that regulates operation clock of each shift register 31 is given to each of the plurality of shift registers 31. In addition, a vertical start signal Spy that starts the operation of the vertical shift register 30 is given to one end of a series circuit of the plurality of shift registers 31.

When the vertical start signal Spy is input to the first shift register 31, output voltages Shift from the plurality of shift registers 31 sequentially fall in response to the timing of the vertical clock signal Ckv only for a predetermined period.

Then, the output voltages Shift from the shift registers 31 are sequentially input to the respective NOR gates 32 which are provided for the respective rows. The result of the NOR operation between the output voltages Shift and the gate signals Gate are output to the buffers 33, respectively. The signal outputs from the buffers 33 are supplied as row selection control signals Vsel to the row selecting lines 13, respectively. The gate signal Gate is for reducing the time width of a pulse in the row selection control signal Vsel.

As shown in FIG. 3, in this embodiment, the plurality of signal output units 20 are provided in association with a plurality of column groups of the light receiving unit 10, respectively. The column groups are divided from the N columns of the light receiving unit 10 so that each of the column groups two or more columns. In other words, the light receiving unit 10 includes a plurality of column groups. Each of the plurality of column groups includes two or more different pixel columns among the N pixel columns. The plurality of signal output units 20 are provided in association with the plurality of column groups, respectively. For example, in the circuit shown in FIG. 3, one column group includes five pixel columns, and one signal output unit 20 is provided in association with the five pixel columns. The output ends of the M pixels 11 in each column of the light receiving unit 10 are connected through the readout line 12 to the signal output unit 20 which is provided in association with the column group including the relevant column (specifically, integrating circuit 21 provided for the relevant column in the signal output unit 20)

Figure 4:
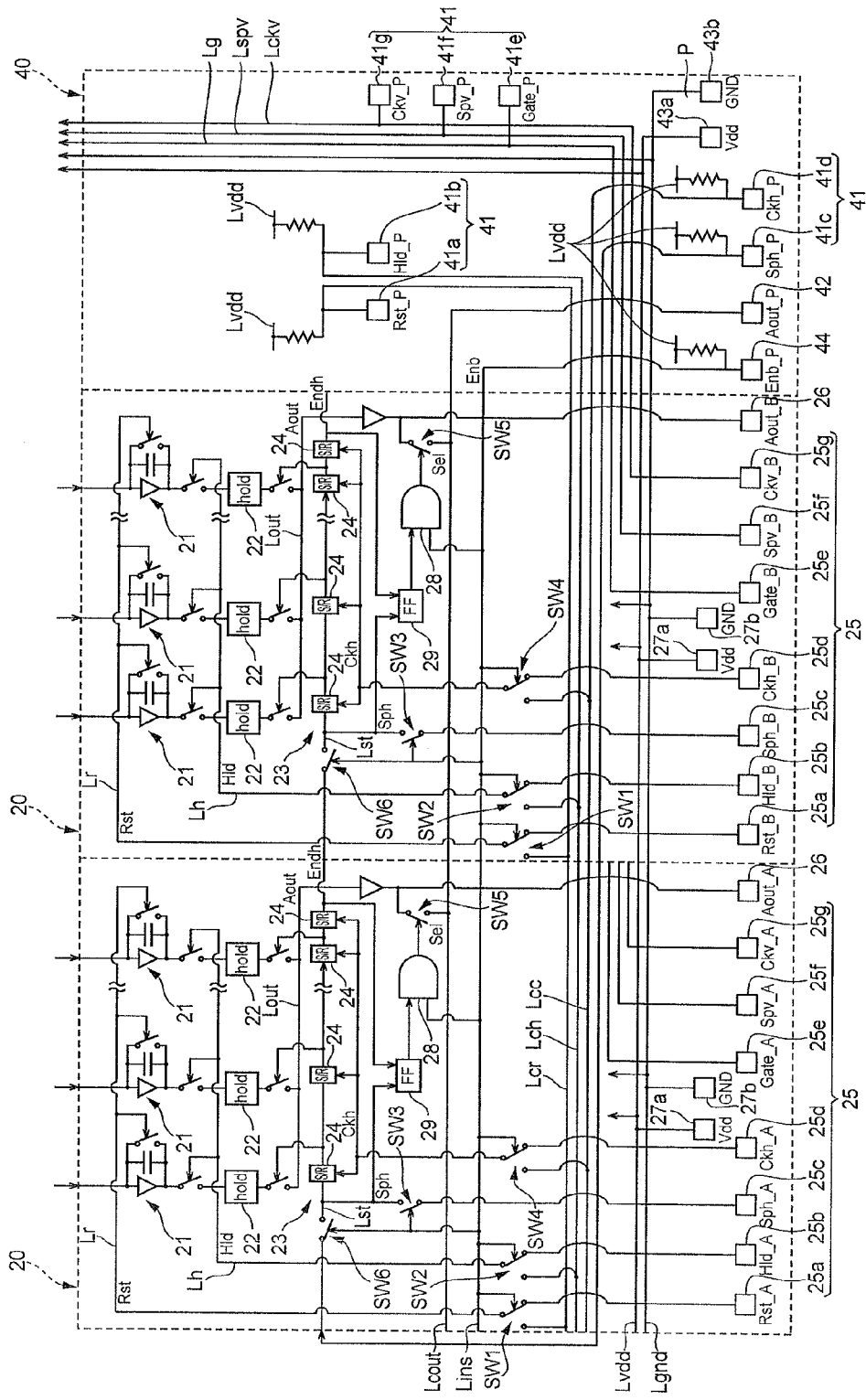
FIG. 4 is a circuit diagram illustrating in detail a structure of the signal output unit 20 and a test terminal electrode unit 40 among the components of the solid-state imaging device 1 shown in FIG. 1.

FIG. 4 is a circuit diagram illustrating in detail the structure of the signal output unit 20 and the test terminal electrode unit 40 among the components of the solid-state imaging device 1 shown in FIG. 1. FIG. 4 shows two signal output units 20 in the vicinity of the vertical shift register 30 (see FIG. 1) among the plurality of signal output units 20.

Each of the plurality of signal output units 20 includes the integrating circuits 21, holding circuits 22, and a horizontal shift register 23. In each signal output unit 20, two or more integrating circuits 21 are provided in association with two or more columns in the column group which is connected to the relevant signal output unit 20, respectively. Each of the integrating circuits 21 includes an input end that is connected to the readout line 12 of the corresponding column. Each of the integrating circuits 21 accumulates the charge that is output from each of the pixels 11 included in the corresponding column through the readout line 12 and outputs a voltage value corresponding to an amount of the accumulated charge from an output end to the corresponding holding circuit 22. The integrating circuits 21 are connected to a reset line Lr. A reset signal Rst is given to the reset line Lr. The reset signal Rst is for instructing switching operation of a switch for discharge in the integrating circuit 21 to reset the integrating circuit 21.

In each signal output unit, two or more holding circuits 22 are provided in association with the integrating circuits 21, respectively. Each of the holding circuits 22 has an input end that is connected to the output end of the corresponding integrating circuit 21 through a switch, holds the voltage value input to the input end, and outputs the held voltage value from an output end to a voltage output line Lout through a switch. Each holding circuit 22 is connected to a holding line Lh. A hold signal Hld is given to the holding line Lh. The hold signal Hld is for instructing switching operation of the respective switches between the holding circuits 22 and the integrating circuits 21 to control the input of the voltage signals to the holding circuits 22.

The horizontal shift register 23 sequentially connects the holding circuits 22 with the voltage output line Lout such that the voltage signals are sequentially output from the holding circuits 22. The horizontal shift register 23 includes shift registers 24 (which are mainly configured with flip-flops) whose number is equal to the number of holding circuits 22. The shift registers 24 are connected in series to each other. An input end of the first shift register 24 is connected to a start line Lst. A horizontal start signal Sph is given to the start line Lst. The horizontal start signal Sph is for starting the operation of the horizontal shift register 23. The input ends of the subsequent shift registers 24 are connected to the output ends of the preceding shift registers 24, respectively. Each of the shift register 24 outputs a signal with a predetermined time delay using the signal input to the input end thereof as a trigger. The output end of each shift register 24 is connected to a control end of the switch provided between the holding circuit 22 in the corresponding column and the voltage output line Lout.

Each of the plurality of signal output units 20 further includes an input terminal electrode group 25. The input terminal electrode group 25 is a first input terminal electrode group according to this embodiment and includes a plurality of terminal electrodes (electrode pads) 25a to 25g for signal input.

The terminal electrode 25a is for inputting the reset signal Rst that resets the integrating circuits 21. The terminal electrode 25b is for inputting the hold signal Hld that controls input of the voltage signals to the holding circuits 22. The terminal electrode 25c is for inputting the horizontal start signal Sph that starts the operation of the horizontal shift register 23. The terminal electrode 25d is for inputting the horizontal clock signal Ckh that regulates the clock of the horizontal shift register 23. The terminal electrodes 25e to 25g are for inputting the gate signal Gate, the vertical start signal Spv, and the vertical clock signal Ckv used in the vertical shift register 30 (see FIG. 3), respectively.

The reset signal terminal electrode 25a is connected to one of two input ends of a switch SW1. An output end of the switch SW1 is connected to the reset line Lr. When the one input end and the output end of the switch SW1 are connected, the reset signal Rst input to the terminal electrode 25a is provided to two or more integrating circuits 21.

The hold signal terminal electrode 25b is connected to one of two input ends of a switch SW2. An output end of the switch SW2 is connected to the holding line Lh. When the one input end and the output end of the switch SW2 are connected, the hold signal Hld input to the terminal electrode 25b controls the input of the voltage signal to each of two or more holding circuits 22.

The horizontal start signal terminal electrode 25c is connected to one end of a switch SW3. The other end of the switch SW3 is connected to the start line Lst. When the switch SW3 is put into a connected state, the horizontal start signal Sph input to the terminal electrode 25c is provided to the first shift register 24 of the horizontal shift register 23.

The horizontal clock signal terminal electrode 25d is connected to one of two input ends of a switch SW4. An output end of the switch SW4 is connected to the shift registers 24. When the one input end and the output end of the switch SW4 are connected, the horizontal clock signal Ckh input to the terminal electrode 25d is provided to the shift registers 24.

The switches SW1, SW2, and SW4 are input switches in this embodiment and are provided in each signal output unit 20 in order to switch an electrode group which is connected with the integrating circuit 21, the holding circuit 22, and the horizontal shift register 23 between the input terminal electrode group 25 and an input terminal electrode group 41, which will be described below.

The lines extending from the gate signal terminal electrode 25e, the vertical start signal terminal electrode 25f, and the vertical clock signal terminal electrode 25g extend to the edge of the signal output unit 20 close to the vertical shift register 30 (see FIG. 3). In addition, the gate signal line Lg, the vertical start signal line Lspv, and the vertical clock signal line Lckv extending from the vertical shift register 30 extend to the boundary between the rightmost signal output unit 20 of the plurality of signal output units 20 and the test terminal electrode unit 40. Therefore, in the rightmost signal output unit 20, the lines extending from the terminal electrodes 25e to 25g are connected to the lines Lg, Lspv, and Lckv extending from the vertical shift register 30, respectively. In the other signal output units 20, the lines extending from the terminal electrodes 25e to 25g are cut at the boundary between the signal output units 20, and the terminal electrodes 25e to 25g are not used. This structure of the terminal electrodes 25e to 25g is formed by manufacturing all of the signal output units 20 with the same pattern.

Each of the plurality of signal output units 20 further includes an output terminal electrode 26, a power supply terminal electrode 27a, and a reference potential terminal electrode 27b. The output terminal electrode 26 is a first output terminal electrode in this embodiment and is for providing output signals Aout which are transmitted from the holding circuits 22 through the voltage output line Lout to the outside of the semiconductor substrate 14. The output terminal electrode 26 is connected to the voltage output line Lout through an amplifying element (amplifier).

The power supply terminal electrode 27a is a first power supply terminal electrode in this embodiment and is for receiving a power supply voltage. The reference potential terminal electrode 27b is for regulating a reference potential. The power supply terminal electrode 27a and the reference potential terminal electrode 27b are respectively connected to a power supply line Lvdd and a reference potential line Lgnd which are provided across the plurality of signal output units 20

The solid-state imaging device 1 according to this embodiment further includes a reset common line Lcr, a holding common line Lch, a clock common line Lcc, a voltage output common line Lcout, and a mode selecting line Lins. These lines are provided across the plurality of signal output units 20. The reset common line Lcr, the holding common line Lch, and the clock common line Lcc form an input signal line in this embodiment. The voltage output common line Lcout forms an output signal line in this embodiment.

The reset common line Lcr is connected to the other end of the two input ends of the switch SW1 in each of the plurality of signal output units 20. The holding common line Lch is connected to the other end of the two input ends of the switch SW2 in each of the plurality of signal output units 20. The clock common line Lcc is connected to the other end of the two input ends of the switch SW4 in each of the plurality of signal output units 20. The mode selecting line Lins is connected to the control end of each of the switches SW1 to SW4 and the operation of each of the switches SW1 to SW4 is controlled by a signal (a mode selection signal Enb which will be described below) provided to the mode selecting line Lins.

The voltage output common line Lcout is connected to the voltage output line Lout through the switch SW5 in each of the plurality of signal output units 20. The switch SW5 is an output switch in this embodiment and is provided in order to switch the connection/disconnection between the holding circuit 22 and the voltage output common line Lcout. The turning-on/off of the switch SW5 is controlled by an output signal Sel from an AND circuit (AND gate) 28. One input end of the AND gate 28 is connected to an output end of a flip-flop circuit 29, and the other input end of the AND gate 28 is connected to the mode selecting line Lins. The horizontal start signal Sph is input to a set terminal of the flip-flop circuit 29 and the last output signal Endh of the horizontal shift register 23 is input to a reset terminal of the flip-flop circuit 29 through another shift register.

As described above, the test terminal electrode unit 40 is provided in a region which is adjacent to the signal output unit 20 closest to the vertical shift register 30. The test terminal electrode unit 40 includes an input terminal electrode group 41 that is provided separately from the input terminal electrode group 25 in each signal output unit 20. The input terminal electrode group 41 is a second input terminal electrode group in this embodiment and includes a plurality of terminal electrodes (electrode pads) 41a to 41g for signal input.

The terminal electrodes 41a to 41g are for inputting the reset signal Rst, the hold signal Hld, the horizontal start signal Sph, the horizontal clock signal Ckh, the gate signal Gate, the vertical start signal Spv, and the vertical clock signal Ckv, respectively. The reset signal terminal electrode 41a is connected to the reset common line Lcr. The hold signal terminal electrode 41b is connected to the holding common line Lch. The clock signal terminal electrode 41d is connected to the clock common line Lcc. Each of the terminal electrodes 41a, 41b, and 41d is connected to the power supply line Lvdd through a resistor.

The gate signal terminal electrode 41e is connected to the gate signal line Lg extending from the vertical shift register 30. The vertical start signal terminal electrode 41f is connected to the vertical start signal line Lspv extending from the vertical shift register 30. The vertical clock signal terminal electrode 41g is connected to the vertical clock signal line Lckv extending from the vertical shift register 30.

The horizontal start signal terminal electrode 41c is connected to the horizontal shift register 23 of the signal output unit 20 which is disposed at an end (hereinafter, referred to as a left end) farthest away from the vertical shift register 30 among the plurality of signal output units 20 through the line which is provided across the plurality of signal output units 20 and the switch SW6. Therefore, when the horizontal start signal Sph is input to the terminal electrode 41c with the switch SW6 being closed, the horizontal shift register 23 of the signal output unit 20 starts to operate. In each of the other signal output units 20, the first shift register 24 of the horizontal shift register 23 is connected to the last shift register 24 of the horizontal shift register 23 in another signal output unit 20 which is adjacent to the far side of the vertical shift register 30 through the switch SW6. When the switch SW6 is in a closed state, each horizontal shift register 23 receives the output signal Endh from the last shift register 24 of the adjacent signal output unit 20 as the horizontal start signal Sph. The control end of the switch SW6 is connected to the mode selecting line Lins and only one of the switches SW3 and SW6 is put into a connected state by the mode selection signal Enb provided to the mode selecting line Lins.

The test terminal electrode unit 40 further includes an output terminal electrode 42 that is provided separately from the output terminal electrodes 26 of the signal output units 20. The output terminal electrode 42 is connected to the voltage output common line Lcout. The test terminal electrode unit 40 further includes a power supply terminal electrode 43a and a reference potential terminal electrode 43b which are provided separately from the power supply terminal electrodes 27a and the reference potential terminal electrode 27bs of the signal output units 20. The power supply terminal electrode 43a is connected to the power supply terminal electrodes 27a of the signal output units 20 through the power supply line Lvdd, and the reference potential terminal electrode 43b is connected to the reference potential terminal electrodes 27b of the signal output units 20 through the reference potential line Lgnd.

The test terminal electrode unit 40 further includes a mode selecting terminal electrode 44. The mode selecting terminal electrode 44 is for inputting the mode selection signal Enb that controls the switches SW1 to SW6 and is connected to the mode selecting line Lins. The mode selecting terminal electrode 44 is connected to the power supply line Lvdd through a resistor.

Figure 5:
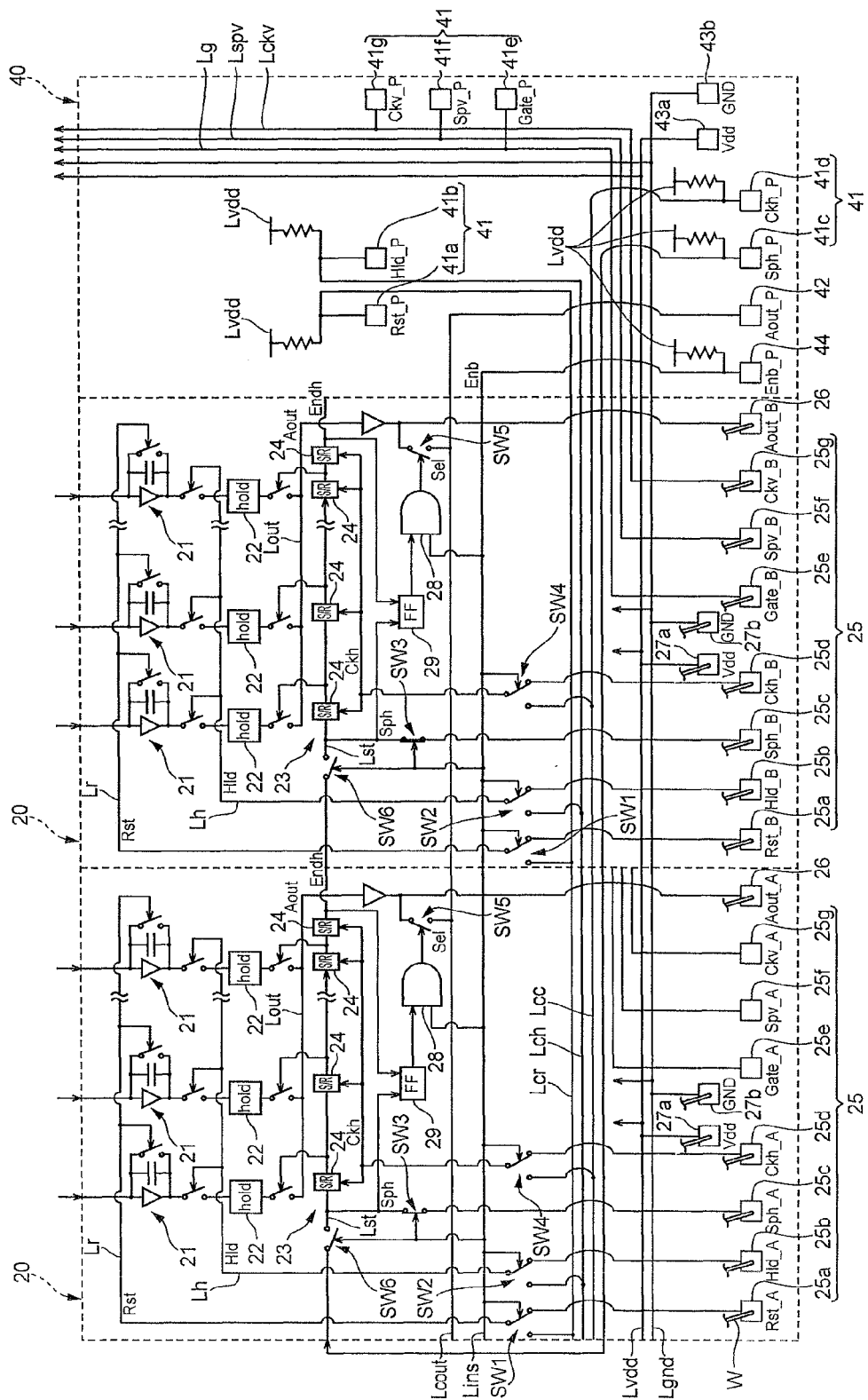
FIG. 5 is a block diagram illustrating a state of the solid-state imaging device 1 in a normal operation mode.
Figure 6:
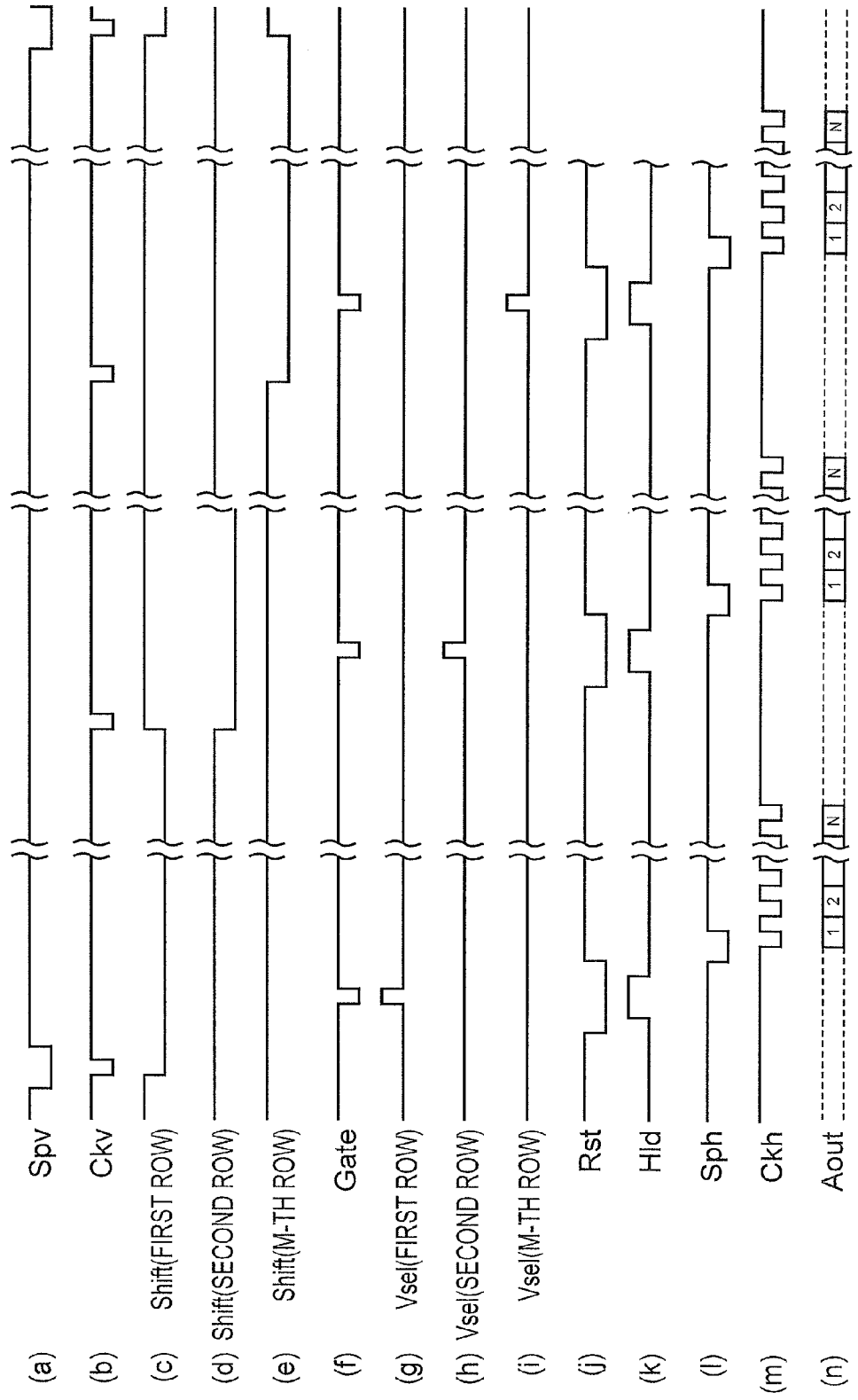
FIG. 6 is a timing chart illustrating signals in the normal operation mode.
Figure 7:
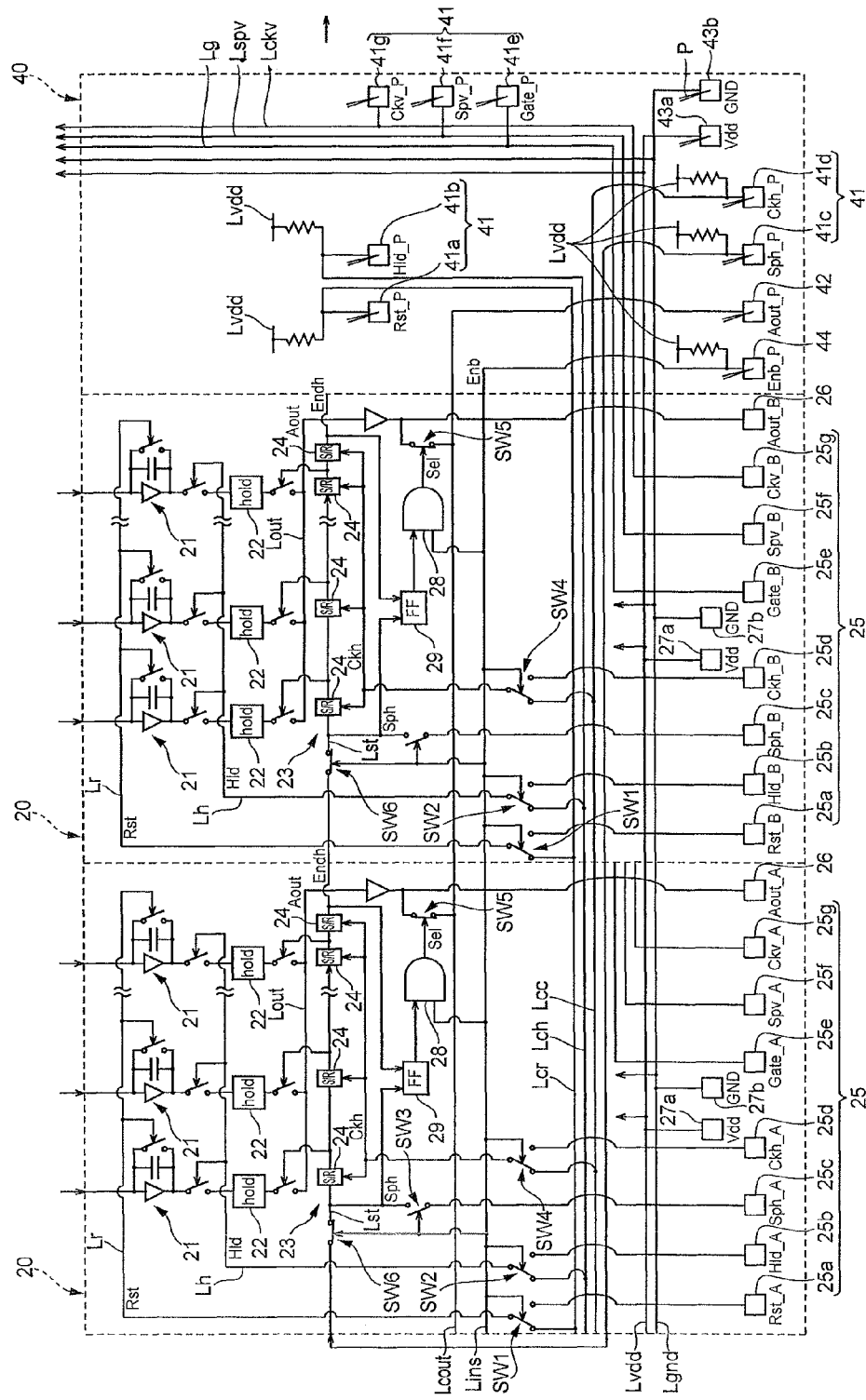
FIG. 7 is a block diagram illustrating a state of the solid-state imaging device 1 in a test mode.
Figure 8:
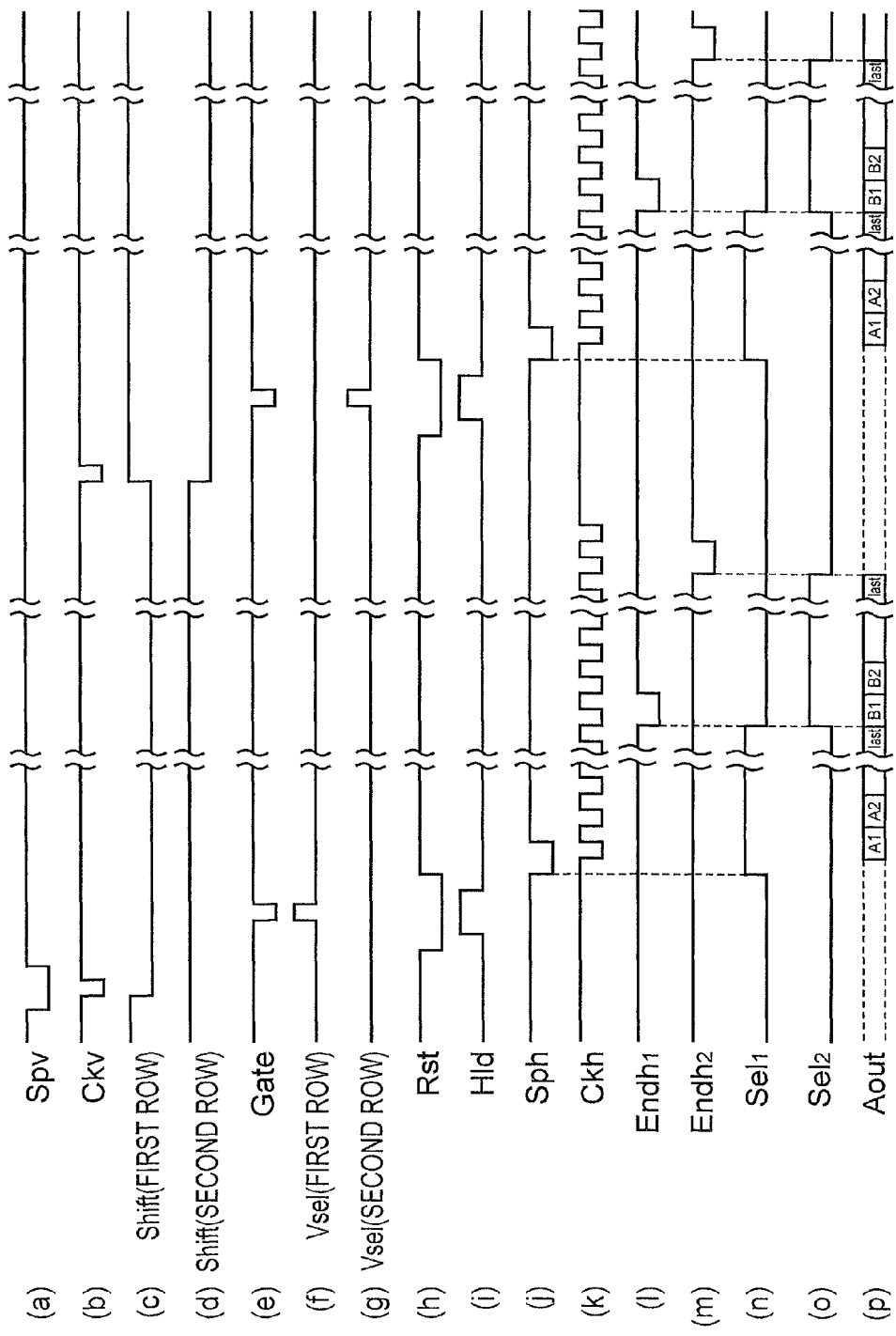
FIG. 8 is a timing chart illustrating signals in a test mode.

Next, the operation of the solid-state imaging device 1 according to this embodiment having the above-mentioned structure will be described. FIG. 5 is a block diagram illustrating a state of the solid-state imaging device 1 (mainly the state of the switches SW1 to SW6. Hereinafter, this state is referred to as a normal operation mode) during a normal operation. FIG. 6 is a timing chart illustrating signals in the normal operation mode. FIG. 7 is a block diagram illustrating a state of the solid-state imaging device 1 (hereinafter, this state is referred to as a test mode) when the functions of the light receiving unit 10, the signal output units 20, and the vertical shift register 30 of the solid-state imaging device 1 are tested by probes. FIG. 8 is a timing chart illustrating signals in the test mode.

First, the normal operation mode of the solid-state imaging device 1 will be described with reference to FIGS. 5 and 6. During the normal operation of the solid-state imaging device 1, as shown in FIG. 5, in all of the signal output units 20, bonding wires W are connected to the reset signal terminal electrode 25a, the hold signal terminal electrode 25b, the horizontal start signal terminal electrode 25c, the horizontal clock signal terminal electrode 25d, the power supply terminal electrode 27a, and the reference potential terminal electrode 27b. Then, the reset signal Rst, the hold signal Hld, the horizontal start signal Sph, the horizontal clock signal Ckh, the power supply voltage Vdd, and the reference potential GND are input from, for example, an external electronic component through the bonding wires W.

In this case, since nothing is connected to the mode selecting terminal electrode 44 of the test terminal electrode unit 40, the potential of the mode selecting line Lins is fixed to the power supply voltage Vdd (that is, an H level). In this case, as shown in FIG. 5, in each of the switches SW1, SW2, and SW4 of each signal output unit 20, one of the two input ends that is connected to the input terminal electrode group 25 and the output end are connected to each other. In addition, the switch SW3 is put into a connected state and the switches SW5 and SW6 are put into an unconnected state.

In this state, first, in the rightmost signal output unit 20, an L-level pulse signal is input as the vertical start signal Spy to the vertical start signal terminal electrode 25f (FIG. 6(a)). This pulse signal is provided to the uppermost shift register 31 (see FIG. 3) of the vertical shift register 30. During this period, that is, during the period for which the vertical start signal Spy is at an L level, an L-level pulse signal is input as the vertical clock signal Ckv to the vertical clock signal terminal electrode 25g (FIG. 6(b)). This pulse signal is provided to the shift registers 31 of the vertical shift register 30. As a result, an output voltage Shift from the uppermost shift register 31 is maintained at an L level until the next pulse signal of the vertical clock signal Ckv is input (FIG. 6(c)).

Then, in each of the plurality of signal output units 20, an L-level voltage is input as the reset signal Rst to the reset signal terminal electrode 25a (FIG. 6(j)). This voltage is provided to each integrating circuit 21. As a result, the reset state of each integrating circuit 21 in each signal output unit 20 is cancelled. During this period, that is, during the period for which the reset signal Rst is at an L level, an H-level signal is input as the hold signal Hld to the hold signal terminal electrode 25b (FIG. 6(k)), and the integrating circuits 21 and the holding circuits 22 are respectively connected to each other by this signal.

Then, in the rightmost signal output unit 20, an L-level pulse signal is input as the gate signal Gate to the gate signal terminal electrode 25e (FIG. 6(f)). This pulse signal is input to each NOR gate 32 (see FIG. 3) of the vertical shift register 30. In this case, the uppermost NOR gate 32 performs a NOR operation on the output voltage Shift from the shift register 31 and the gate signal Gate and outputs an H-level pulse signal as the operation result. This pulse signal is provided as the row selection control signal Vsel to the row selecting line 13 in the relevant row through the buffer 33 (FIG. 6(g)). As a result, the readout switch SWa of each of the pixels 11 in the first row of the light receiving unit 10 is closed and the charge generated from the photodiode PD is moved to the integrating circuit 21 for each column through the readout line 12.

Since the reset state is cancelled, each integrating circuit 21 accumulates charge and outputs a voltage value corresponding to the amount of the accumulated charge to the holding circuit 22. The voltage value is held by the holding circuit 22.

In this way, the charge from each of the pixels 11 in the first row of the light receiving unit 10 is held by the holding circuit 22. Then, in each of the plurality of signal output units 20, the hold signal Hld returns to the L level (FIG. 6(k)) and the reset signal Rst returns to the H level (FIG. 6(j)). As a result, in each of the signal output units 20, the integrating circuits 21 are reset and the integrating circuits 21 and the holding circuits 22 are respectively disconnected from each other.

Then, in each of the plurality of signal output units 20, an L-level pulse signal is input as the horizontal start signal Sph to the horizontal start signal terminal electrode 25c (FIG. 6(l)). This pulse signal is provided to the first shift register 24 of the horizontal shift register 23. This pulse signal is also provided to the flip-flop circuit 29. However, since the potential of the mode selecting line Lins is fixed to an H level, the switch SW5 is maintained in the unconnected state.

Then, when the horizontal start signal Sph is at the L level, an L-level pulse signal is input as the horizontal clock signal Ckh to the horizontal clock signal terminal electrode 25d (FIG. 6(m)). This pulse signal is provided to the shift registers 24 of the horizontal shift register 23. Then, the output voltages from the shift registers 24 sequentially connect the holding circuits 22 with the voltage output line Lout, and the voltage values held by the holding circuits 22 are sequentially provided as the output signals Aout to the output terminal electrode 26 (FIG. 6(n)). In this way, the output signals Aout corresponding to the first row of the light receiving unit 10 are extracted from the output terminal electrode 26 through the bonding wire W.

Then, when the L-level pulse signal is input as the vertical clock signal Ckv to the terminal electrode 25g again (FIG. 6(b)), the output voltage Shift from the uppermost shift register 31 returns to the H level (FIG. 6(c)) and the output voltage Shift from the next shift register 31 becomes an L level (FIG. 6(d)). Then, the reset signal Rst and the hold signal Hld are respectively input to the terminal electrodes 25a and 25b in the same way as described above and an L-level pulse signal is input as the gate signal Gate to the gate signal terminal electrode 25e (FIG. 6(f)). This pulse signal is input to each NOR gate 32 of the vertical shift register 30. When the gate signal Gate input to the NOR gate 32 is at an H level, the output signal from the uppermost NOR gate 32 returns to the L level. In addition, the next NOR gate 32 performs a NOR operation on the output voltage Shift from the shift register 31 and the gate signal Gate and outputs an H-level pulse signal. This pulse signal is provided as the row selection control signal Vsel to the row selecting line 13 in the relevant row through the buffer 33 (FIG. 6(h)). As a result, the readout switch SWa of each of the pixels 11 in the second row of the light receiving unit 10 is closed and the charge generated from the photodiode PD is moved to the integrating circuit 21 for each column through the readout line 12. Thereafter, similarly to the first row, the horizontal start signal Sph and the horizontal clock signal Ckh are input (FIGS. 6(l) and 6(m)), and the output signals Aout corresponding to the second row of the light receiving unit 10 are extracted from the output terminal electrode 26 through the bonding wire W (FIG. 6(n)).

The above-mentioned operation is sequentially repeated on row by row basis. When an M-th pulse signal is input as the vertical clock signal Ckv (FIG. 6(b)), the output voltage Shift from the lowermost shift register 31 becomes an H level (FIG. 6(e)). When a pulse signal is input as the gate signal Gate (FIG. 6(f)), the output signal from the lowermost NOR gate 32 is provided as the row selection control signal Vsel to the row selecting line 13 in an M-th row through the buffer 33 (FIG. 6(i)). In the other rows, similarly, when the output signals Aout corresponding to the M-th row of the light receiving unit are extracted from the output terminal electrode 26 (FIG. 6(n)), the acquisition of data corresponding to one frame is completed.

Next, the test mode of the solid-state imaging device 1 will be described with reference to FIGS. 7 and 8. This mode is for testing the functions of the light receiving unit 10, the plurality of signal output units 20, and the vertical shift register 30 before wires are bonded to each terminal electrode of each signal output unit 20.

First, as shown in FIG. 7, in the test terminal electrode unit 40, test probes P are brought into contact with the reset signal terminal electrode 41a, the hold signal terminal electrode 41b, the horizontal start signal terminal electrode 41c, the horizontal clock signal terminal electrode 41d, the gate signal terminal electrode 41e, the vertical start signal terminal electrode 41f, the vertical clock signal terminal electrode 41g, the output terminal electrode 42, the power supply terminal electrode 43a, the reference potential terminal electrode 43b, and the mode selection signal terminal electrode 44, respectively. Then, the reset signal Rst, the hold signal Hld, the horizontal start signal Sph, the horizontal clock signal Ckh, the gate signal Gate, the vertical start signal Spv, the vertical clock signal Ckv, the power supply voltage Vdd, the reference potential GND, and the mode selection signal Enb are input to the terminal electrodes through the test probes P, respectively.

In this case, an L-level voltage is applied as the mode selection signal Enb to the mode selecting terminal electrode 44. As shown in FIG. 7, each of the switches SW1, SW2, and SW4 of each signal output unit 20 are operated such that one of the two input ends thereof that is connected to each of the common lines Lcr, Lch, and Lcc is connected to the output end. In addition, the switch SW3 is put into an unconnected state and the switch SW6 is put into a connected state.

In this state, first, in the test terminal electrode unit 40, an L-level pulse signal is input as the vertical start signal Spv to the vertical start signal terminal electrode 41f (FIG. 8(a)). This pulse signal is provided to the uppermost shift register 31 (see FIG. 3) of the vertical shift register 30. During this period, that is, during the period for which the vertical start signal Spy is at an L level, an L-level pulse signal is input as the vertical clock signal Ckv to the vertical clock signal terminal electrode 41g (FIG. 8(*b*)). This pulse signal is provided to the shift registers 31 of the vertical shift register 30. As a result, the output voltage Shift from the uppermost shift register 31 is maintained at an L level until the next pulse signal of the vertical clock signal Ckv is input (FIG. 8(*c*)).

Then, in the test terminal electrode unit 40, an L-level voltage is input as the reset signal Rst to the input reset signal terminal electrode 41a (FIG. 8(*h*)). This voltage is provided to each integrating circuit 21 of each signal output unit 20 through the reset common line Lcr. As a result, the reset state of each integrating circuit 21 in each of the plurality of signal output units 20 is cancelled. During this period, that is, during the period for which the reset signal Rst is at an L level, an H-level signal is input as the hold signal Hld to the hold signal terminal electrode 41b (FIG. 8(*i*)). This signal is provided to each signal output unit 20 through the holding common line Lch. As a result, in each of the plurality of signal output units 20, the integrating circuits 21 and the holding circuits 22 are respectively connected to each other.

Then, in the test terminal electrode unit 40, an L-level pulse signal is input as the gate signal Gate to the gate signal terminal electrode 41e (FIG. 8(*e*)). This pulse signal is input to each NOR gate 32 (see FIG. 3) of the vertical shift register 30. In this case, the uppermost NOR gate 32 performs a NOR operation on the output voltage Shift from the shift register 31 and the gate signal Gate and outputs an H-level pulse signal. This pulse signal is provided as the row selection control signal Vsel to the row selecting line 13 in the relevant row through the buffer 33 (FIG. 8(*f*)). As a result, the readout switch SWa of each of the pixels 11 in the first row of the light receiving unit 10 is closed and the charge generated from the photodiode PD is moved to the integrating circuit 21 for each column through the readout line 12.

Since the reset state is cancelled, each integrating circuit 21 accumulates charge and outputs a voltage value corresponding to the amount of the accumulated charge to the holding circuit 22. The voltage value is held by the holding circuit 22.

In this way, the charge from each of the pixels 11 in the first row of the light receiving unit 10 is held by the holding circuit 22. Then, in the test terminal electrode unit 40, the hold signal Hld returns to the L level (FIG. 8(*i*)) and the reset signal Rst returns to the H level (FIG. 8(*h*)). As a result, in each of the plurality of signal output units 20, the integrating circuits 21 are reset and the integrating circuits 21 and the holding circuits 22 are respectively disconnected from each other.

Then, in the test terminal electrode unit 40, an L-level pulse signal is input as the horizontal start signal Sph to the horizontal start signal terminal electrode 41c (FIG. 8(*j*)). This pulse signal is provided to the first shift register 24 of the horizontal shift register 23 in the leftmost signal output unit 20 among the plurality of signal output units 20. This pulse signal is also provided to the flip-flop circuit 29 of the signal output unit 20, and the voltage input from the flip-flop circuit 29 to one input end of the AND gate 28 becomes an L-level voltage. In the test mode, since the potential of the mode selecting line Lins connected to the other input end of the AND gate 28 is an L level, the output signal Sel of the AND gate 28 becomes an H level (FIG. 8(*n*)). As a result, the switch SW5 of the signal output unit 20 is put into a connected state.

When the horizontal start signal Sph becomes an L level, in the test terminal electrode unit 40, an L-level pulse signal is input as the horizontal clock signal Ckh to the horizontal clock signal terminal electrode 41d (FIG. 8(*k*)). This pulse signal is provided to the shift registers 24 of the horizontal shift register 23. As a result, in the leftmost signal output unit 20, the output signals from the shift registers 24 sequentially connect the holding circuits 22 with the voltage output line Lout and the voltage values held by the holding circuits 22 are sequentially provided as the output signals Aout to the voltage output common line Lcout (A1, A2, ... in FIG. 8(*p*)). In this way, the output signals Aout corresponding to the first row in the leftmost column group of the light receiving unit 10 are extracted from the output terminal electrode 42 through the test probe P.

The signal Endh (FIG. 8(*l*)) output from the last shift register 24 of the leftmost signal output unit 20 is also provided to the flip-flop circuit 29 of the signal output unit 20 through another shift register 24. Therefore, after all of the output signals Aout are output from the holding circuits 22 of the signal output unit 20, the output voltage from the flip-flop circuit 29 becomes an H level and the output voltage Sel from the AND gate 28 becomes an L level. Therefore, the switch SW5 is switched into an unconnected state (FIG. 8(*n*)).

This signal Endh is provided as the horizontal start signal Sph to a signal output unit 20 (that is, the second signal output unit 20 from the left end) adjacent to the signal output unit 20. Therefore, the output signal Sel from the AND gate 28 of the second signal output unit 20 from the left end becomes an H level (FIG. 8(*o*)) and the switch SW5 of the second signal output unit 20 is put into a connected state. In the second signal output unit 20, the horizontal start signal Sph is provided to the first shift register 24 through the switch SW6. In this case, the horizontal clock signal Ckh is continuously input from the terminal electrode 41d (FIG. 8(*k*)). Therefore, in the second signal output unit 20 from the left end, the output signals from the shift registers 24 sequentially connect the holding circuits 22 with the voltage output line Lout and the voltage values held by the holding circuits 22 are sequentially output as the output signals Aout to the voltage output common line Lcout (B1, B2, ... in FIG. 8(*p*)). In this way, the output signals Aout corresponding to the first row in the second column group from the left end in the light receiving unit 10 are extracted from the output terminal electrode 42 through the test probe P.

The signal Endh (FIG. 8(*m*)) output from the last shift register 24 of the second signal output unit 20 from the left end is also provided to the flip-flop circuit 29 of the signal output unit 20 through another shift register 24. Therefore, after all of the output signals Aout are output from the holding circuits 22 of the second signal output unit 20, the output voltage of the flip-flop circuit 29 becomes an H level and the output voltage Sel from the AND gate 28 becomes an L level. Therefore, the switch SW5 is switched into an unconnected state (FIG. 8(*n*)). In addition, the signal Endh is provided to a signal output unit 20 (that is, the third signal output unit 20 from the left end) adjacent to the second signal output unit 20.

Thereafter, the same operation as described above is performed on a plurality of signal output units 20 including the third signal output unit 20 from the left end to the rightmost signal output unit 20. The output signals Aout corresponding to the first row of the corresponding column group of the light receiving unit 10 are extracted from the output terminal electrode 42 through the test probe P.

Then, when the L-level pulse signal is input as the vertical clock signal Ckv to the terminal electrode 41g again (FIG. 8(*b*)), the output voltage Shift from the uppermost shift register 31 returns to the H level (FIG. 8(*c*)) and the output voltage Shift from the next shift register 31 becomes an H level (FIG. 8(*d*)). Then, the reset signal Rst and the hold signal Hld are respectively input to the terminal electrodes 41a and 41b in the same way as described above, and an L-level pulse signal is input as the gate signal Gate to the gate signal terminal electrode 41e (FIG. 8(e)). This pulse signal is input to each NOR gate 32 of the vertical shift register 30. When the gate signal Gate input to the NOR gate 32 is at an H level, the output signal from the uppermost NOR gate 32 returns to the L level. The next NOR gate 32 performs a NOR operation on the output voltage Shift from the shift register 31 and the gate signal Gate and outputs an H-level pulse signal. This pulse signal is provided as the row selection control signal Vsel to the row selecting line 13 in the relevant row through the buffer 33 (FIG. 8(g)). As a result, the readout switch SWa of each of the pixels 11 in the second row of the light receiving unit 10 is closed and the charge generated from the photodiode PD is moved to the integrating circuit 21 for each column through the readout line 12. Thereafter, similarly to the first row, the horizontal start signal Sph and the horizontal clock signal Ckh are input (FIGS. 8(j) and 8(k)), and the output signals Aout corresponding to the second row in each column group of the light receiving unit 10 are extracted from the output terminal electrode 42 through the test probe P (FIG. 8(p)).

The above-mentioned operation is sequentially repeated on row by row basis. When the output signals Aout corresponding to the M-th row of the light receiving unit 10 are extracted from the output terminal electrode 42, the test of the functions of the entire region of the light receiving unit 10, the plurality of signal output units 20, and the vertical shift register 30 is completed.

According to the solid-state imaging device 1 of this embodiment having the above-mentioned structure, it is possible to test the operation of the light receiving unit 10 and the signal output units 20 by bringing the test probes P into contact with the input terminal electrode group 41 and the output terminal electrode 42 which are separately provided for a test, in stead of the input terminal electrode group 25 and the output terminal electrode 26 which are provided in each of the plurality of signal output units 20. Therefore, the number of test probes P that are brought into contact with the terminal electrodes is reduced, as compared to the method in which the test probes P are brought into contact with the terminal electrodes 25a to 25d of all of the signal output units 20 simultaneously. Hence, even when the light receiving unit 10 has a large area, it is possible to accurately and easily test the light receiving unit 10 and the plurality of signal output units 20.

In addition, the solid-state imaging device 1 according to this embodiment includes the vertical shift register 30 that controls the output of charge from the pixels 11 on row by row basis. The plurality of signal output units 20 is arranged adjacent to one side of the light receiving unit 10 extending along the row direction and the vertical shift register 30 is arranged adjacent to another side of the light receiving unit 10 extending along the column direction. In such a case, as in this embodiment, the input terminal electrode group 41 and the output terminal electrode 42 may be arranged in a region (in this embodiment, a region adjacent to the signal output unit 20 disposed at the right end) which is adjacent to the signal output unit 20 closest to the vertical shift register 30 among the plurality of signal output units 20. This arrangement makes it possible to effectively arrange the common lines Lcr, Lch, Lcc, and Lcout and appropriately arrange the input terminal electrode group 41 and the output terminal electrode 42 so as not to affect the arrangement of the signal output units 20 or the vertical shift register 30.

In addition, as in this embodiment, the terminal electrode 41c for the horizontal start signal Sph in the input terminal electrode group 41 may be connected to the horizontal shift register 23 of the signal output unit 20 (in this embodiment, the signal output unit 20 disposed at the left end) which is disposed at the end among the plurality of signal output units 20. In the test mode in which the horizontal start signal Sph is input to the terminal electrode 41c, the horizontal shift register 23 of each of the other signal output units 20 may receive the output signal Endh from the last stage of the horizontal shift register 23 of an adjacent signal output unit 20 as the horizontal start signal Sph. In this way, the output signals Aout from the plurality of signal output units 20 can be sequentially extracted from the output terminal electrode 42 (see FIG. 8(p)).

In the solid-state imaging device 1 according to this embodiment, each of the plurality of signal output units 20 includes the power supply terminal electrode 27a for inputting the power supply voltage Vdd. In this case, the solid-state imaging device 1 may further include the power supply terminal electrode 43a for receiving the power supply voltage Vdd, separately from the power supply terminal electrode 27a of each of the plurality of signal output units 20. The power supply terminal electrodes 27a and 43a may be connected to each other by the power supply line Lvdd which is provided across the plurality of signal output units 20. According to this structure, in the test mode that tests the light receiving unit 10 and the plurality of signal output units 20, the number of test probes P for supplying the power supply voltage Vdd is reduced, and it is possible to perform the test with ease.

As in this embodiment, the solid-state imaging device 1 may include the switch SW5 that is provided in each signal output unit 20 in order to switch the connection/disconnection between the holding circuit 22 and the voltage output common line Lcout. According to this configuration, in the test mode, when a certain signal output unit 20 outputs the output signal Aout, it is possible to disconnect the other signal output units 20 from the voltage output common line Lcout. Therefore, it is possible to prevent an influence on the output signal Aout passing through the voltage output common line Lcout. For example, as in this embodiment, when the operation of the horizontal shift register 23 starts (specifically, when the horizontal start signal Sph becomes an L level: see FIG. 8(j)), the switch SW5 connects the holding circuit 22 and the voltage output common line Lcout. When the operation of the horizontal shift register 23 is completed (specifically, when the last shift register 24 outputs the signal Endh: see FIGS. 8(l) and 8(m)), the switch SW5 disconnects the holding circuit 22 from the voltage output common line Lcout. In this way, it is possible to appropriately obtain the above-mentioned effect.

(Modifications)

Next, modifications of the solid-state imaging device 1 according to the first embodiment will be described. FIG. 9 is a block diagram schematically illustrating the horizontal shift register 23 provided in each of the plurality of signal output units 20. In (a) of FIG. 9, a case in which the first shift register 24 is disposed at the left end, that is, the scanning of the horizontal shift register 23 is performed in a direction to the test terminal electrode unit 40 as in the first embodiment, is shown. On the contrary, in (b) of FIG. 9, a case in which the first shift register 24 is disposed at the right end, that is, the scanning of the horizontal shift register 23 is performed in a direction departing away from the test terminal electrode unit 40, is shown. The scanning direction of the horizontal shift register 23 may be changed between the direction shown in (a) of FIG. 9 and the direction shown in (b) of FIG. 9. Next, the reason will be described.

The scanning direction of the horizontal shift register 23 in the first embodiment is the direction shown in (a) of FIG. 9. In (a) of FIG. 10, a plan view schematically illustrating an aspect of the normal operation mode of the solid-state imaging device 1 is shown. In (a) of FIG. 10, an arrow AR1 indicates the scanning direction and the scanning start and end points of the horizontal shift register 23 in each signal output unit 20. An arrow AR2 indicates the scanning direction and the scanning start and end points of the vertical shift register 30. An arrow AR3 indicates the order in which the signals Aout corresponding to each pixel 11 are output. In the normal operation mode, the horizontal start signal Sph is input to each of the signal output units 20. Therefore, even when the horizontal shift registers 23 are scanned in this direction, it is possible to output the signals Aout with high efficiency, as shown in (a) of FIG. 10.

However, the test mode has the following problems. In (b) of FIG. 10, a plan view schematically illustrating an aspect of the test mode of the solid-state imaging device 1 is shown. In (b) of FIG. 10, an arrow BR1 indicates the scanning direction and the scanning start and end points of the horizontal shift register 23s in all of the plurality of signal output units 20. An arrow BR2 indicates the scanning direction and the scanning start and end points of the vertical shift register 30. An arrow BR3 indicates the order in which the signals Aout corresponding to each pixel 11 are output.

When the scanning direction of the horizontal shift register 23 is the direction shown in (a) of FIG. 9, as shown in (b) of FIG. 10, in the test mode, first, the horizontal start signal Sph is input to the leftmost signal output unit 20 and the horizontal shift registers 23 are sequentially scanned from the leftmost signal output unit 20 to the rightmost signal output unit 20. Therefore, a line for transmitting the horizontal start signal Sph from the test terminal electrode unit 40 to the leftmost signal output unit 20 is needed. This line is provided across the plurality of signal output units 20. Therefore, a large space is needed and the line is likely to hinder the extension of other lines.

FIG. 11 is a plan view schematically illustrating aspects of the normal operation mode ((a) of FIG. 11) and the test mode ((b) of FIG. 11) of the solid-state imaging device 1 when the scanning direction of the horizontal shift register 23 is changed to the direction shown in (b) of FIG. 9. As shown in (a) of FIG. 11, in the normal operation mode, even when the scanning direction of the horizontal shift register 23 is changed, substantially the same configuration as that shown in (a) FIG. 10 is obtained. However, as shown in (b) of FIG. 11, in the test mode, the horizontal start signal Sph is input to the rightmost signal output unit 20 and the horizontal shift registers 23 are sequentially scanned from the rightmost signal output unit 20 to the leftmost signal output unit 20. Therefore, the length of the line for transmitting the horizontal start signal Sph from the test terminal electrode unit 40 is reduced. As a result, it is easy to provide other lines and it is possible to reduce a space.

As such, since the scanning direction of the horizontal shift register 23 can be changed, it is possible to reduce the length of the line for connecting the terminal electrode 41c for the horizontal start signal Sph in the input terminal electrode group 41 and the horizontal shift register 23 of the signal output unit 20 disposed at the end. In addition, since the scanning direction of the vertical shift register 30 can be changed, it is possible to reduce the length of the line.

(Second Embodiment)

Figure 12:
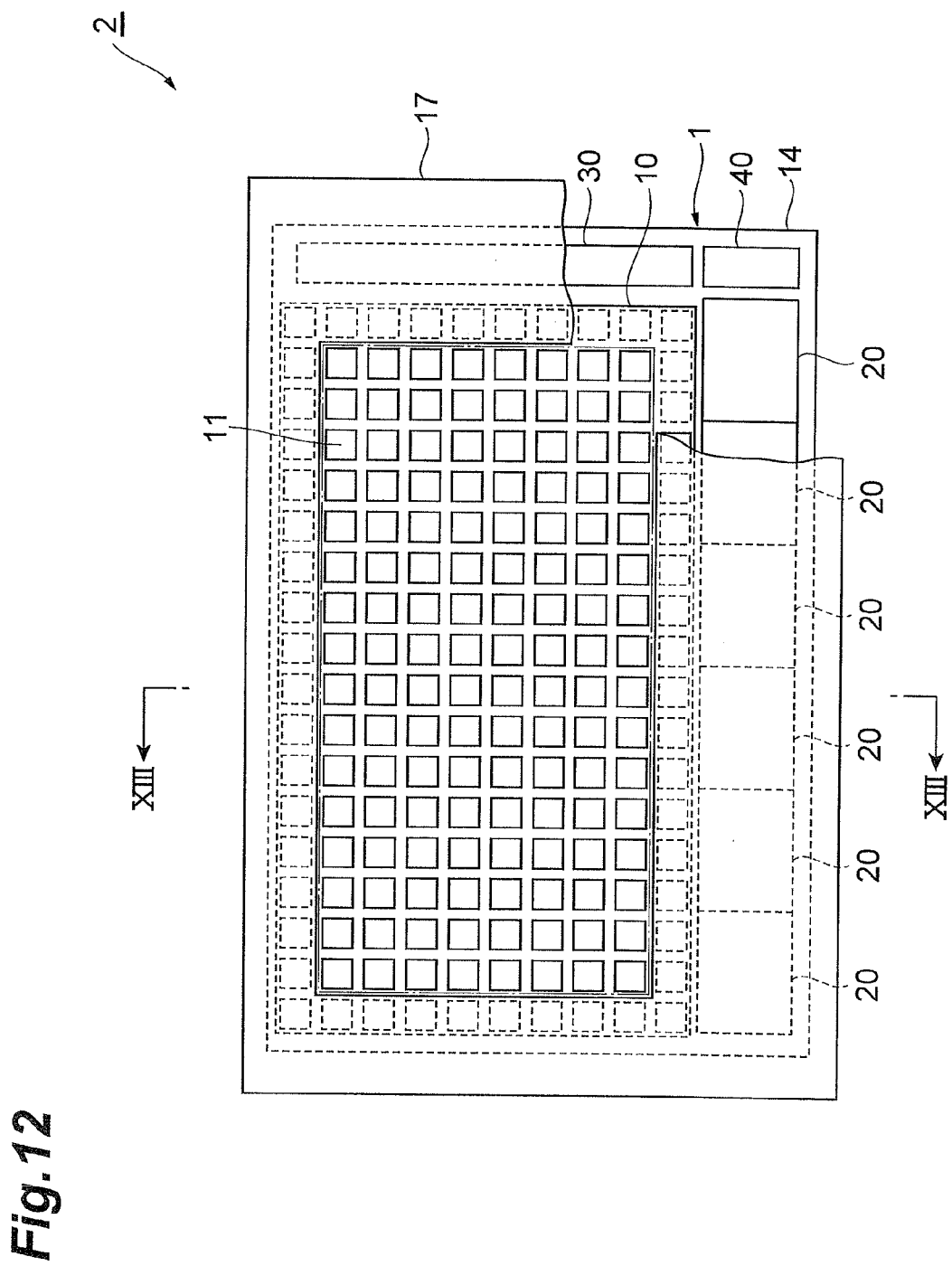
FIG. 12 is a plan view illustrating the structure of a radiological imaging apparatus 2 according to a second embodiment.
Figure 13:
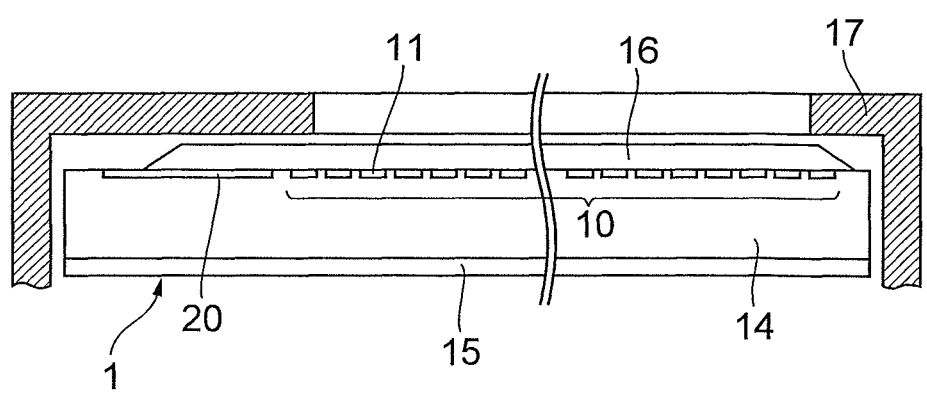
FIG. 13 is a side cross-sectional view illustrating a cross section of the radiological imaging apparatus 2 taken along the line XIII-XIII of FIG. 12.

FIG. 12 is a plan view illustrating the structure of a radiological imaging apparatus 2 according to a second embodiment of the invention. FIG. 13 is a side cross-sectional view illustrating the cross section of the radiological imaging apparatus 2 taken along the line XIII-XIII of FIG. 12.

As shown in FIGS. 12 and 13, the radiological imaging apparatus 2 includes the solid-state imaging device 1 according to the first embodiment, a scintillator 16 (see FIG. 13; not shown in FIG. 12) that is provided on the light receiving unit 10 of the solid-state imaging device 1, and a radiation shielding unit 17. The scintillator 16 generates scintillation light according to incident radiation, such as X-rays, converts a radiation image into an optical image, and outputs the optical image to the light receiving unit 10. The scintillator 16 is provided so as to cover the light receiving unit 10 or it is provided on the light receiving unit 10 by vapor deposition. The radiation shielding unit 17 is made of a material with low radiation transmittance, such as lead. The radiation shielding unit 17 covers the edge of the semiconductor substrate 14 and prevents the incidence of radiation on, for example, the signal output unit 20. In the semiconductor substrate 14, the pixels formed along the edge of the light receiving unit 10 are covered with the radiation shielding unit 17, and configure light-shielding pixels into which no light enters and from which no charge is generated.

The radiological imaging apparatus 2 according to this embodiment includes the solid-state imaging device 1 according to the first embodiment. Therefore, it is possible to accurately and easily test the light receiving unit 10 and the signal output units 20 of the solid-state imaging device 1. As a result, it is possible to provide the radiological imaging apparatus 2 with high reliability.

(Third Embodiment)

Figure 14:
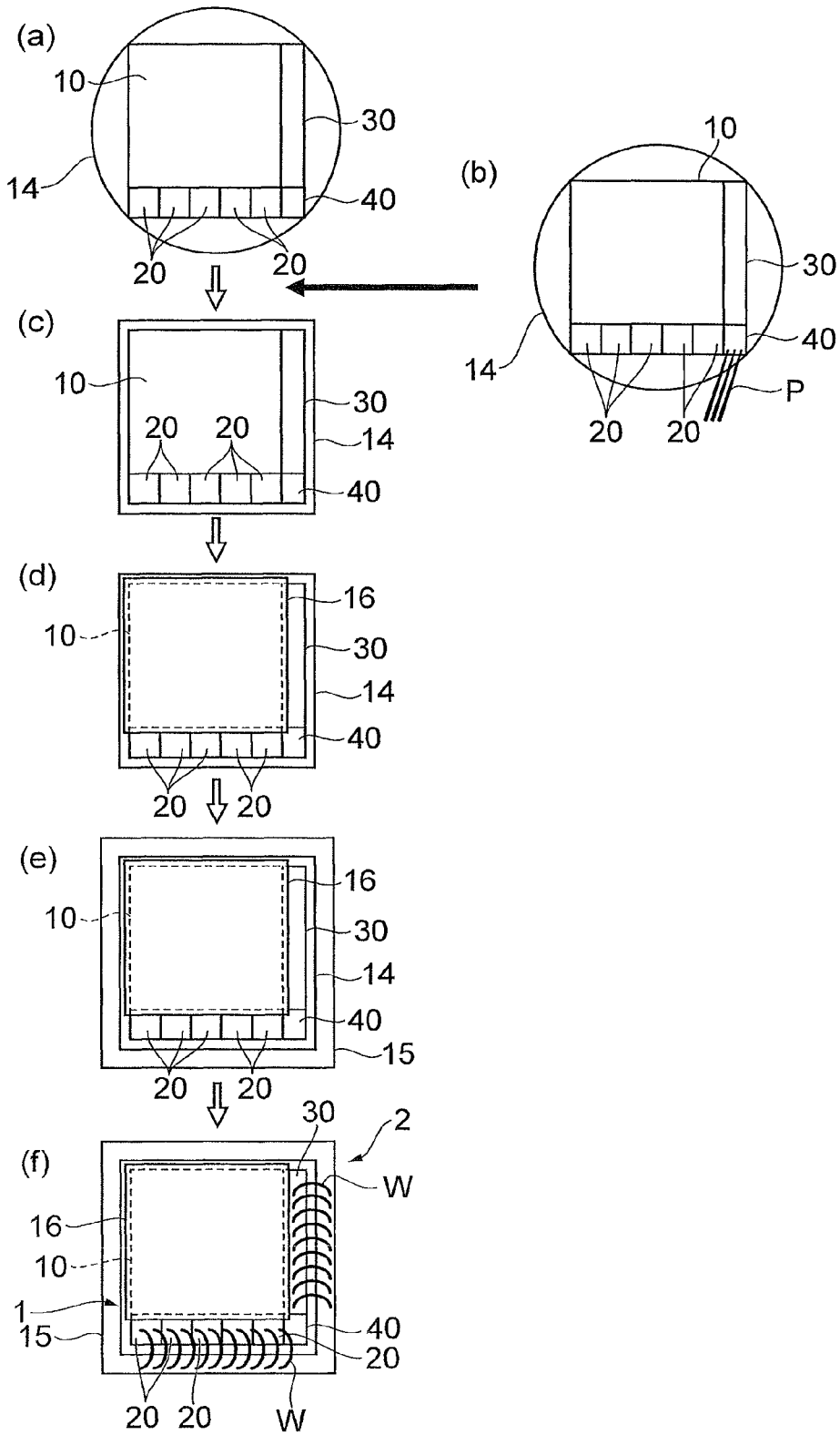
FIG. 14 is diagram illustrating each step for manufacturing the radiological imaging apparatus 2.

Next, as a third embodiment of the invention, a method of manufacturing the radiological imaging apparatus 2 according to the second embodiment will be described. The manufacturing method includes a method of manufacturing the solid-state imaging device 1 according to the first embodiment and a method of testing the solid-state imaging device 1. FIG. 14 is a diagram illustrating each step of manufacturing the radiological imaging apparatus 2.

First, as shown in (a) of FIG. 14, the light receiving unit 10, the plurality of signal output units 20, the vertical shift register 30, and the test terminal electrode unit 40 described in the first embodiment are formed on the main surface of a wafer-shaped semiconductor substrate 14 by a general semiconductor process technique (forming step).

That is, as the light receiving unit 10, M×N (M and N are integers equal to or greater than 2) pixels 11 (see FIG. 1) each having the photodiode PD and the readout switch SWa are formed on the semiconductor substrate 14. In addition, a plurality of signal output units 20 is formed adjacent to one side of the light receiving unit 10 extending in the row direction and in association with a plurality of column groups each of which has two or more columns and which are divided from N columns. Specifically, as shown in FIG. 4, as each signal output unit 20, two or more integrating circuits 21 that are provided in association with two or more columns included in the corresponding column group, accumulates the charge output from the pixels 11 in the corresponding columns, and convert the charge into a voltage signal, two or more holding circuits 22 that are connected to the output ends of the two or more integrating circuits 21, respectively, the horizontal shift register 23 that causes the two or more holding circuits 22 to sequentially output the voltage signal Aout, the input terminal electrode group 25 including the terminal electrodes 25a to 25g, the output terminal electrode 26, the power supply terminal electrode 27a, the reference potential terminal electrode 27b, the AND gate 28, and the flip-flop circuit 29 are formed in a region which will be each of the plurality of signal output units 20 on the semiconductor substrate 14. In addition, the vertical shift register 30 shown in FIG. 2 is formed adjacent to another side of the light receiving unit 10 extending in the column direction.

As the test terminal electrode unit 40, the input terminal electrode group 41 including the terminal electrodes 41a to 41g shown in FIG. 4, the output terminal electrode 42, the power supply terminal electrode 43a, and the reference potential terminal electrode 43b, and the mode selecting terminal electrode 44 are formed in a region adjacent to the signal output unit 20 (that is, the rightmost signal output unit 20) that is closest to the vertical shift register 30 among the plurality of signal output units 20.

In the forming step, the switches SW1 to SW6 are formed in each signal output unit 20. In addition, the common lines Lcr, Lch, and Lcc that connect the switches SW1, SW2 and SW4 of each signal output unit 20 and the terminal electrodes 41a, 41b, and 41d, respectively, the voltage output common line Lcout that connects the holding circuit 22 of each signal output unit 20 and the output terminal electrode 42, the power supply line Lvdd that connects the power supply terminal electrodes 27a and 43a, and the reference potential line Lgnd that connects the reference potential terminal electrodes 27b and 43b are formed across the plurality of signal output units 20.

In the forming step, the horizontal start signal terminal electrode 41c is connected to the first shift register 24 of the horizontal shift register 23 in the signal output unit 20 (for example, the leftmost signal output unit 20) disposed at the end among the plurality of signal output units 20 through the switch SW6. Among the other signal output units 20, the first shift register 24 of the horizontal shift register 23 of a signal output unit 20 is connected to the last shift register 24 of the horizontal shift register 23 of an adjacent signal output unit 20 through the switch SW6.

Then, the operation of the light receiving unit 10, the plurality of signal output units 20, and the vertical shift register 30 are tested, and the semiconductor substrate 14 in which the light receiving unit 10, the plurality of signal output units 20, and the vertical shift register 30 are normally operated is selected from a plurality of semiconductor substrates 14 (test step).

That is, as shown in (b) of FIG. 14, the test probes P are brought into contact with the test terminal electrode unit 40 and signals are input thereto. In this case, the plurality of signal output units 20 is changed to the test mode. Specifically, as shown in FIG. 7, the test probes P are brought into contact with the power supply terminal electrode 43a and the reference potential terminal electrode 43b, respectively, and the power supply voltage Vdd and the reference potential GND are input thereto. In addition, another test probe P is brought into contact with the mode selecting terminal electrode 44 and the mode selection signal Enb is input to the mode selecting terminal electrode 44, thereby changing the switches SW1 to SW6 to the test mode. At the same time, other test probes P are brought into contact with the terminal electrodes 41a to 41g of the input terminal electrode group 41, and the reset signal Rst, the hold signal Hld, the horizontal start signal Sph, the horizontal clock signal Ckh, the gate signal Gate, the vertical start signal Spv, and the vertical clock signal Ckv are given to the terminal electrodes 41a to 41g of the input terminal electrode group 41. In this way, the above-mentioned operation in the test mode is performed in the plurality of signal output units 20 and the vertical shift register 30, and another test probe P is brought into contact with the output terminal electrode 42 to acquire the voltage signal Aout. In this way, it is possible to test the operation of the light receiving unit 10 and the plurality of signal output units 20.

In the test step, the scanning direction of the horizontal shift register 23 in each signal output unit 20 may be different from that during the normal operation as in the modification of the first embodiment (see FIGS. 9 to 11). This is because it is possible to reduce the length of the line for connecting the horizontal start signal terminal electrode 41c and the horizontal shift register 23 of the signal output unit 20 disposed at the end.

Then, as shown in (c) of FIG. 14, a peripheral portion of the light receiving unit 10, the plurality of signal output units 20, the vertical shift register 30, and the test terminal electrode unit 40 in the semiconductor substrate 14 is cut by dicing (cutting step). The test step shown in (b) of FIG. 14 may be performed after the cutting step.

Then, as shown in (d) of FIG. 14, the scintillator 16 is provided on the light receiving unit 10 (scintillator attaching step). In this case, as the scintillator 16, a scintillator panel may be provided so as to cover the light receiving unit 10, or a scintillator material may be formed on the light receiving unit 10 by vapor deposition. In addition, in this case, the scintillator 16 is provided such that the terminal electrodes 25a to 25g, 26, 27a, and 27b of each of the plurality of signal output units 20 are exposed.

Then, as shown in (e) of FIG. 14, the semiconductor substrate 14 is fixed to a wiring substrate 15 and the terminal electrodes of each signal output unit 20 are connected to a wiring pattern that is prepared outside the semiconductor substrate 14, via the bonding wires W (wire bonding step). In this case, as shown in FIG. 5, in each of the plurality of signal output units 20, the bonding wires W are connected to the reset signal terminal electrode 25a, the hold signal terminal electrode 25b, the horizontal start signal terminal electrode 25c, the horizontal clock signal terminal electrode 25d, the output terminal electrode 26, the power supply terminal electrode 27a, and the reference potential terminal electrode 27b. The bonding wires W are connected to the gate signal terminal electrode 25e, the vertical start signal terminal electrode 25f, and the vertical clock signal terminal electrode 25g only in the signal output unit 20 which is disposed closest to the vertical shift register 30 among the plurality of signal output units 20.

The solid-state imaging device 1 and the radiological imaging apparatus 2 including the solid-state imaging device 1 are manufactured by the above-mentioned steps.

According to the methods of manufacturing and testing the solid-state imaging device 1 and the radiological apparatus 2, the following advantages are obtained. That is, in the test step, the test probes P are not brought into contact with the input terminal electrode group 25 and the output terminal electrode 26 provided in each of the plurality of signal output units 20, but are brought into contact with the input terminal electrode group 41 and the output terminal electrode 42 which are separately provided for the test step. In this way, it is possible to test the operation of the light receiving unit 10, the signal output unit 20, and the vertical shift register 30. Therefore, the number of test probes P that are brought into contact with the terminal electrodes is reduced, as compared to the method in which the test probes P are brought into contact with the terminal electrodes 25a to 25d of all of the signal output units 20 simultaneoutly. As a result, even when the light receiving unit 10 has a large area, it is possible to accurately and easily test the light receiving unit 10, the plurality of signal output units 20, and the vertical shift register 30.

In addition, in this embodiment, the input terminal electrode group 41 and the output terminal electrode 42 is arranged in the region (test terminal electrode unit 40) which is adjacent to the signal output unit 20 closest to the vertical shift register 30 among the plurality of signal output units 20. Therefore, it is possible to effectively arrange the common lines Lcr, Lch, Lcc, and Lcout and appropriately arrange the input terminal electrode group 41 and the output terminal electrode 42 so as not to affect the arrangement of the signal output units 20 or the vertical shift register 30.

In this embodiment, the terminal electrode 41c for the horizontal start signal Sph in the input terminal electrode group 41 may be connected to the horizontal shift register 23 of the signal output unit 20 (in this embodiment, the signal output unit 20 disposed at the left end) closest to the end. In the test mode, the output signal Endh from the last stage of the horizontal shift register 23 of an adjacent signal output unit 20 may be provided as the horizontal start signal Sph to the horizontal shift registers of the other signal output units 20. In this way, the output signals Aout from the plurality of signal output units 20 can be sequentially extracted from the output terminal electrode 42.

In this embodiment, in the forming step, the power supply terminal electrode 43a receiving the power supply voltage Vdd may be formed in the test terminal electrode unit 40, and the power supply terminal electrodes 27a of the plurality of signal output units 20 and the power supply terminal electrode 43a may be connected to each other by the power supply line Lvdd. According to this structure, in the test step, the number of test probes P for supplying the power supply voltage Vdd is reduced and it is possible to perform the test with ease.

Furthermore, in this embodiment, in the forming step, the switch SW5 for switching the connection/disconnection between the holding circuit 22 and the voltage output common line Lcout may be formed in each of the signal output units 20. In this way, in the test step, it is possible to disconnect other signal output units 20 from the voltage output common line Lcout. Therefore, it is possible to prevent an influence on the output signal Aout passing through the voltage output common line Lcout.

The solid-state imaging device and the method of manufacturing the same, the radiological imaging apparatus and the method of manufacturing the same, and the method of testing the solid-state imaging device according to the invention are not limited to the above-described embodiments, but various modifications and changes of the invention can be made. In each of the above-described embodiments, the test terminal electrode unit 40 is arranged adjacent to the signal output unit 20 which is disposed at the right end among the plurality of signal output units 20. However, for example, the second input terminal electrode group or the output terminal electrode according to the invention may be arranged adjacent to the signal output unit which is disposed at the left end among the plurality of signal output units, or it may be arranged in other regions on the semiconductor substrate.

In the third embodiment, the test step is performed before the scintillator attaching step. However, in the invention, the test step may be performed after the scintillator attaching step.

REFERENCE SIGNS LIST

1: SOLID-STATE IMAGING DEVICE
2: RADIOLOGICAL IMAGING APPARATUS
10: LIGHT RECEIVING UNIT
11: PIXEL
12: READOUT LINE
13: ROW SELECTING LINE
14: SEMICONDUCTOR SUBSTRATE
15: WIRING SUBSTRATE
16: SCINTILLATOR
17: RADIATION SHIELDING UNIT
20: SIGNAL OUTPUT UNIT
21: INTEGRATING CIRCUIT
22: HOLDING CIRCUIT
23: HORIZONTAL SHIFT REGISTER
24: SHIFT REGISTER
25, 41: INPUT TERMINAL ELECTRODE GROUP
25a to 25g, 41a to 41g: TERMINAL ELECTRODE
26, 42: OUTPUT TERMINAL ELECTRODE
27a, 43a: POWER SUPPLY TERMINAL ELECTRODE
27b, 43b: REFERENCE POTENTIAL TERMINAL ELECTRODE
28: AND GATE
29: FLIP-FLOP CIRCUIT
30: VERTICAL SHIFT REGISTER
31: SHIFT REGISTER
32: NOR GATE
33: BUFFER
40: TEST TERMINAL ELECTRODE UNIT
44: MODE SELECTING TERMINAL ELECTRODE
Aout: OUTPUT SIGNAL
Ckh: HORIZONTAL CLOCK SIGNAL
Ckv: VERTICAL CLOCK SIGNAL
Enb: MODE SELECTION SIGNAL
Endh: OUTPUT SIGNAL
Gate: GATE SIGNAL
Hld: HOLD SIGNAL
Rst: RESET SIGNAL
Sph: HORIZONTAL START SIGNAL
Spv: VERTICAL START SIGNAL
Vsel: ROW SELECTION CONTROL SIGNAL
Lcc: CLOCK COMMON LINE
Lch: HOLDING COMMON LINE
Lcout: VOLTAGE OUTPUT COMMON LINE
Lcr: RESET COMMON LINE
Lgnd: REFERENCE POTENTIAL LINE
Lh: HOLDING LINE
Lins: MODE SELECTING LINE
Lout: VOLTAGE OUTPUT LINE
Lr: RESET LINE
Lst: START LINE
Lvdd: POWER SUPPLY LINE
P: TEST PROBE
PD: PHOTODIODE
SW1 to SW6: SWITCH
SWa: READOUT SWITCH
W: BONDING WIRE

The invention claimed is:

1. A solid-state imaging device comprising:
a light receiving unit that includes M×N (M and N are integers equal to or greater than 2) pixels which are two-dimensionally arranged in a matrix of M rows and N columns and each of which includes a photodiode;
a plurality of signal output units that is provided in association with a plurality of column groups, respectively, wherein the column groups are divided from the N columns and each of the column groups includes two or more columns; and
a vertical shift register that controls charge outputs from the pixels on row by row basis,
wherein each of the plurality of signal output units includes:
two or more integrating circuits that are provided in association with the two or more columns in a corresponding column group, each of which accumulates charge output from the pixels in a corresponding column, and converts the charge into a voltage signal;
two or more holding circuits that are connected to output ends of the two or more integrating circuits, respectively;
a horizontal shift register that causes the two or more holding circuits to sequentially output voltage signals;
a first input terminal electrode group including a plurality of terminal electrodes for inputting a reset signal that resets the integrating circuits, a hold signal that controls input of voltage signals to the holding circuits, a horizontal start signal that starts operation of the horizontal shift register, a horizontal clock signal that regulates clock of the horizontal shift register; and
a first output terminal electrode that provides output signals from the holding circuits,
the solid-state imaging device further includes:
a second input terminal electrode group that is provided separately from the first input terminal electrode group and includes a plurality of terminal electrodes for receiving the reset signal, the hold signal, the horizontal start signal, and the horizontal clock signal, respectively;
input switches that are provided in each signal output unit in order to switch an electrode group which is connects with the integrating circuits, the holding circuits, and the horizontal shift register, between the first and second input terminal electrode groups;
a second output terminal electrode that is provided separately from the first output terminal electrode and provides the output signals;
an input signal line that is provided across the plurality of signal output units in order to connect the input switches in each signal output unit with the second input terminal electrode group (except for a terminal electrode for the horizontal start signal); and
an output signal line that is provided across the plurality of signal output units in order to connect the holding circuits in each signal output unit with the second output terminal electrode.

2. The solid-state imaging device according to claim 1, wherein the plurality of signal output units are arranged adjacent to one side of the light receiving unit extending along a row direction,
the vertical shift register is arranged adjacent to another side of the light receiving unit extending in a column direction, and
the second input terminal electrode group and the second output terminal electrode are arranged in a region which is adjacent to a signal output unit closest to the vertical shift register among the plurality of signal output units.

3. The solid-state imaging device according to claim 1, wherein the terminal electrode for the horizontal start signal in the second input terminal electrode group is connected to the horizontal shift register of a signal output unit which is disposed at an end among the plurality of signal output units, and
when the horizontal start signal is input to the terminal electrode, the horizontal shift register of another signal output unit receives an output from a last stage of the horizontal shift register of an adjacent signal output unit as the horizontal start signal.

4. The solid-state imaging device according to claim 3, wherein, in each of the signal output units, a scanning direction of the horizontal shift register is variable.

5. The solid-state imaging device according to claim 1, wherein each of the plurality of signal output units further includes a first power supply terminal electrode for inputting a power supply voltage,
the solid-state imaging device further includes a second power supply terminal electrode that is provided separately from the first power supply terminal electrode provided in each of the plurality of signal output units and receives the power supply voltage, and
the first and second power supply terminal electrodes are connected to each other by a line that is provided across the plurality of signal output units.

6. The solid-state imaging device according to claim 1, further comprising:
an output switch that is provided in each of the signal output units in order to switch connection/disconnection between the holding circuit and the output signal line.

7. The solid-state imaging device according to claim 6, wherein, when operation of the horizontal shift register starts, the output switch connects the holding circuits with the output signal line, and
when the operation of the horizontal shift register is completed, the output switch disconnects the holding circuits from the output signal line.

8. A radiological imaging apparatus comprising:
the solid-state imaging device according to claim 1; and
a scintillator that is provided on the light receiving unit, generates scintillation light according to incident radiation, converts a radiation image into an optical image, and outputs the optical image to the light receiving unit.

9. A method of manufacturing a solid-state imaging device, wherein the solid-state imaging device includes:
a light receiving unit that includes M×N (M and N are integers equal to or greater than 2) pixels which are two-dimensionally arranged in a matrix of M rows and N columns and each of which includes a photodiode,
a plurality of signal output units that are provided in association with a plurality of column groups, respectively, wherein the column groups are divided from the N columns and each of the column groups includes two or more columns; and
a vertical shift register that controls charge outputs from the pixels on row by row basis,
the method comprising:
a forming step of forming, in each region which will be each of the plurality of signal output units on a semiconductor substrate, two or more integrating circuits that are provided in association with the two or more columns in a corresponding column group, respectively and each of which accumulates charge output from the pixels in the corresponding column, and converts the charge into a voltage signal, two or more holding circuits that are connected to output ends of the two or more integrating circuits, respectively, a horizontal shift register that causes the two or more holding circuits to sequentially output voltage signals, a first input terminal electrode group including a plurality of terminal electrodes for inputting a reset signal that resets the integrating circuits, a hold signal that controls input of the voltage signals to the holding circuits, a horizontal start signal that starts operation of the horizontal shift register, and a horizontal clock signal that regulates clock of the horizontal shift register, and a first output terminal electrode that provides output signals from the holding circuits, and forming the light receiving unit and the vertical shift register on the semiconductor substrate;

a test step of testing operation of the light receiving unit and the plurality of signal output units and selecting the semiconductor substrate that is normally operated; and a wire bonding step of connecting the first input terminal electrode group and the first output terminal electrode of each signal output unit in the semiconductor substrate selected in the test step to a wiring pattern that is prepared outside the semiconductor substrate, using wire bonding, wherein, in the forming step, a second input terminal electrode group including a plurality of terminal electrodes for receiving the reset signal, the hold signal, the horizontal start signal, and the horizontal clock signal is formed separately from the first input terminal electrode group; input switches that switch an electrode group which is connected with the integrating circuits, the holding circuits, and the horizontal shift register between the first and second input terminal electrode groups are formed in each signal output unit; a second output terminal electrode that provides the output signal is formed separately from the first output terminal electrode; and an input signal line that connects the input switches in each signal output unit with the second input terminal electrode group (except for a terminal electrode for the horizontal start signal) and an output signal line that connects the holding circuits in each signal output unit with the second output terminal electrode are formed across the plurality of signal output units, and in the test step, the input switches are switched to the second input terminal electrode group; probes are brought into contact with the second input terminal electrode group; the reset signal, the hold signal, the horizontal start signal and the horizontal clock signal are given to the second input terminal electrode group; and another probe is brought into contact with the second output terminal electrode to acquire voltage signals, thereby testing operation of the light receiving unit and the plurality of signal output units.

10. The method of manufacturing a solid-state imaging device according to claim 9, wherein, in the forming step, each of the plurality of signal output units is formed adjacent to one side of the light receiving unit extending along a row direction, the vertical shift register is formed adjacent to another side of the light receiving unit extending along a column direction, and the second input terminal electrode group and the second output terminal electrode are formed in a region which is adjacent to a signal output unit closest to the vertical shift register among the plurality of signal output units.

11. The method of manufacturing a solid-state imaging device according to claim 9, wherein, in the forming step, the terminal electrode for the horizontal start signal in the second input terminal electrode group is connected to the horizontal shift register of a signal output unit which is disposed at an end among the plurality of signal output units, and in the test step, the horizontal shift register of another signal output unit receives an output from a last stage of the horizontal shift register of an adjacent signal output unit as the horizontal start signal.

12. The method of manufacturing a solid-state imaging device according to claim 11, wherein, in each signal output unit, a scanning direction of the horizontal shift register in the test step is different from that of the horizontal shift register in a normal operation.

13. The method of manufacturing a solid-state imaging device according to claim 9, wherein, in the forming step, a first power supply terminal electrode for inputting a power supply voltage is formed in each region which will be each of the plurality of signal output units on the semiconductor substrate, a second power supply terminal electrode that provides the power supply voltage is formed separately from the first power supply terminal electrode, and a line that connects the first and second power supply terminal electrodes is formed across the plurality of signal output units.

14. The method of manufacturing a solid-state imaging device according to claim 9, wherein, in the forming step, an output switch that switch connection/disconnection between the holding circuits and the output signal line is further formed in each region which will be each of the plurality of signal output units on the semiconductor substrate.

15. The method of manufacturing a solid-state imaging device according to claim 14, wherein, in the test step, when operation of the horizontal shift register starts, the output switch connects the holding circuits with the output signal line, and when the operation of the horizontal shift register is completed, the output switch disconnects the holding circuits from the output signal line.

16. A method of manufacturing a radiological imaging apparatus comprising:

the method of manufacturing a solid-state imaging device according to claim 9; and a scintillator attaching step of providing, on the light receiving unit, a scintillator that generates scintillation light according to incident radiation, converts a radiation image into an optical image, and outputs the optical image to the light receiving unit, wherein the scintillator attaching step is performed before or after the test step.

17. A method of testing a solid-state imaging device, wherein the solid-state imaging device includes:

a light receiving unit that includes M×N (M and N are integers equal to or greater than 2) pixels which are two-dimensionally arranged in a matrix of M rows and N columns and each of which includes a photodiode;

a plurality of signal output units that are provided in association with a plurality of column groups, respectively, wherein the column groups are divided from the N columns and each of the column groups includes two or more columns; and a vertical shift register that controls charge outputs from the pixels on row by row basis, and wherein each of the plurality of signal output units includes:

two or more integrating circuits that are provided in association with the two or more columns in a corresponding column group, respectively, each of which accumulates charge output from the pixels in the corresponding column, and converts the charge into a voltage signal;

two or more holding circuits that are connected to output ends of the two or more integrating circuits, respectively, a horizontal shift register that causes the two or more holding circuits to sequentially output voltage signals;

a first input terminal electrode group including a plurality of terminal electrodes for inputting a reset signal that resets the integrating circuit, a hold signal that controls input of the voltage signal to the holding circuits, a horizontal start signal that starts operation of the horizontal shift register, and a horizontal clock signal that regulates clock of the horizontal shift register; and a first output terminal electrode that provides output signals from the holding circuits, the method comprising:

forming, separately from the first input terminal electrode group, a second input terminal electrode group including a plurality of terminal electrodes for receiving the reset signal, the hold signal, the horizontal start signal, and the horizontal clock signal;

forming, in each signal output unit, input switches that switch an electrode group which is connected with the integrating circuits, the holding circuits, and the horizontal shift register, between the first and second input terminal electrode groups;

forming, separately from the first output terminal electrode, a second output terminal electrode that provides the output signals;

forming an input signal line that connects the input switches in each signal output unit with the second input terminal electrode group (except for a terminal electrode for the horizontal start signal) and an output signal line that connects the holding circuits in each signal output unit with the second output terminal electrode, across the plurality of signal output units; and switching the input switches to the second input terminal electrode group and bringing probes into contact with the second input terminal electrode group to provide the reset signal, the hold signal, the horizontal start signal and the horizontal clock signal to the second input terminal electrode group, and bringing another probe into contact with the second output terminal electrode to acquire the voltage signal, thereby testing operation of the light receiving unit and the plurality of signal output units.

* * * * *

UNITED STATES PATENT AND TRADEMARK OFFICE
CERTIFICATE OF CORRECTION

PATENT NO. : 8,653,466 B2  
APPLICATION NO. : 13/256896  
DATED : February 18, 2014  
INVENTOR(S) : Fujita et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this

Twenty-ninth Day of September, 2015

Michelle K. Lee  
*Director of the United States Patent and Trademark Office*